US007495023B2

(12) United States Patent
Cohen et al.

(10) Patent No.: US 7,495,023 B2
(45) Date of Patent: *Feb. 24, 2009

(54) THIO SEMICARBAZONE AND SEMICARBOZONE INHIBITORS OF CYSTEINE PROTEASES AND METHODS OF THEIR USE

(75) Inventors: Fred E. Cohen, San Francisco, CA (US); Xiaohui Du, Los Angeles, CA (US); Chun Guo, Shenyang (CN); James H. McKerrow, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 361 days.

This patent is subject to a terminal disclaimer.

(21) Appl. No.: 11/084,626

(22) Filed: Mar. 18, 2005

(65) Prior Publication Data

US 2005/0182121 A1    Aug. 18, 2005

Related U.S. Application Data

(63) Continuation of application No. 10/431,714, filed on May 8, 2003, now Pat. No. 6,897,240.

(60) Provisional application No. 60/449,058, filed on Feb. 20, 2003, provisional application No. 60/379,366, filed on May 8, 2002.

(51) Int. Cl.
*A61K 31/38* (2006.01)
*C07D 333/12* (2006.01)

(52) U.S. Cl. ............... 514/438; 514/444; 514/471; 549/75; 549/59; 549/494

(58) Field of Classification Search ............ 549/75, 549/59, 494; 514/438, 444, 471, 44
See application file for complete search history.

(56) References Cited

U.S. PATENT DOCUMENTS

| | | | |
|---|---|---|---|
| 4,385,055 A | 5/1983 | Klayman et al. | |
| 4,440,771 A | 4/1984 | Scovill et al. | |
| 4,657,903 A | 4/1987 | Scovill et al. | |
| 4,739,069 A | 4/1988 | Klayman et al. | |
| 6,008,362 A * | 12/1999 | Commons et al. | 546/331 |
| 6,897,240 B2 * | 5/2005 | Cohen et al. | 514/582 |
| 7,319,110 B2 * | 1/2008 | Lange et al. | 514/383 |
| 2003/0045568 A1 * | 3/2003 | Altamura et al. | 514/438 |

OTHER PUBLICATIONS

Stone et al., 1976, CAS: 84:54228.*
Shaar et al., 1975, CAS: 83:173023.*
Zhou et al., 2000, CAS: 133: 207771.*
Lukevics et al., 1996, CAS: 124: 193285.*
Daiku et al., 1995, CAS: 122: 187591.*
Kumari et al., 1994, CAS: 121:57592.*
Deng et al., 1981, CAS: 95: 132756.*
Umar et al., 1969, CAS: 70: 2052.*
Duca et al., 1952, CAS: 46: 39723.*
Schuler et al., 1952, CAS: 46: 6397.*
Bonaldo, Myrna C., et al.; Characterization and Expression of Proteases during *Trypanosoma cruzi* Metacyclogenesis; Experimental Prasitology 1991 pp. 44-51 vol. 73.
Bromme, Dieter, et al.; "Peptidyl vinyl sulphones: a new class of potent and selective cysteine protease inhibitors"; Biochem. J. 1996 pp. 85-89 vol. 315.
Castineiras et al., "Structural and spectral characterization of two 1-phenyl-1,2-propanedione bis{N(4)-alkylthiosemicarbazones}" CAS Accession No. 132:78174 (1999) (Abstract).
Cerecetto, Hugo, et al.; "1,2,5-Oxadiazole N-Oxide Derivatives and Related Compounds as Potential Antitrypanosomal Drugs: Structure-Activity Relationships"; J. Med. Chem. 1999 pp. 1941-1950 vol. 42.
Cerecetto, Hugo, et al.; "Synthesis and anti-trypanosomal activity of novel 5-nitro-2-furaldehyde and 5-nitrothiophene-2-carboxaldehyde semicarbazone derivatives"; II Farmaco 1998 pp. 89-94 vol. 53.
Cerecetto, Hugo, et al.; "Synthesis and antitrypanosomal evaluation of E-isomers of 5-nitro-2-furaldehyde and 5-nitrothiophene-2-carboxaldehyde semicarbazone derivatives Structure-activity relationships"; Eur. J. Med. Chem. 2000 pp. 343-350 vol. 35.
Cheng et al., "A preliminary note on the relation between structure and antischistosomal activity of nitrofurazones" CAS Accession No. 59:75319 (1963) (Abstract).
Colwell et al., "Preparation and antimalarial activity of compounds related to dypnone guanylhydrazone" CAS Accession No. 74:64038 (1971) (Abstract).
Das, Lopamudra, et al.; "Successful Therapy of Lethal Murine Visceral Leishmaniasis with Cystatin Involves Up-Regulation of Nitric Oxide and a Favorable T Cell Response"; The Journal of Immunology 2000 pp. 4020-4028.
Dimmock et al., "Some aryl semicarbazones possessing anticonvulsant activities" CAS Accession No. 123:297 (1995) (Abstract).
Dimmock, J.R., et al.; "Anticonvulsant Activities of 4-Bromobenzaldehyde Semicarbazone"; Epilepsia 1994 pp. 648-655 vol. 35 No. 3.
Dimmock, Jonathan R., et al.; "Anticonvulsant Activities of 4-(4'-Fluorophenoxy) Benzaldehyde Semicarbazone"; Drug Development Research 1999 pp. 112-125 vol. 46.
Engel, Juan C., et al.; "Cysteine Protease Inhibitors Cure an Experimental *Trypanosoma cruzi* Infection"; J. Exp. Med. 1998 pp. 725-734 vol. 188 No. 4.

(Continued)

*Primary Examiner*—Rei-tsang Shiao
(74) *Attorney, Agent, or Firm*—Townsend and Townsend and Crew LLP

(57) ABSTRACT

The present invention relates to thio semicarbazone and semicarbazone inhibitors of cysteine proteases and methods of using such compounds to prevent and treat protozoan infections such as trypanosomiasis, malaria and leishmaniasis. The compounds also find use in inhibiting cysteine proteases associated with carcinogenesis, including cathepsins B and L.

7 Claims, 18 Drawing Sheets

OTHER PUBLICATIONS

Harth, Guenter, et al.; "Peptide-fluoromethyl ketones arrest intracellular replication and intercellular transmission of *Trypanosoma cruzi*"; Molecular and Biochemical Parasitology 1993 pp. 17-24 vol. 58.

Humphlett et al., "Antimalarials. IX. Antitubercular drugs. 1. Preparation of ketones from γ-diethylaminobutyronitrile and aromatic grignard reagents and their conversion to diamides" CAS Accession No. 43:109 (1949) (Abstract).

Iskander et al., "Coordination compounds of hydrazine derivatives with transition metals. XIX. Redox reactions of copper (II) salts with thiosemicarbazide and hydrazine-s-methyl dithiocarboxylate Schiff bases" CAS Accession No. 94:113576 (1981) (Abstract).

Jain et al., "Possible antiamebic agents" CAS Accession No. 54:56152 (1960) (Abstract).

Kachru et al., "Search for new amebicides. I" CAS Accession No. 52:34983 (1958) (Abstract).

Klayman et al., "2-acetylpyridine thiosemicarbazones. 1. A new class of potential antimalarial agents" CAS Accession No. 91:151061 (1979) (Abstract).

May et al., "Attempts to find new antimalarials. XV. Phenanthrene. 31. Amino alcohols of the typ CH(OH) CH2NR2 derived from 3-chloro-6-acetylphenanthrene" CAS Accession No. 41:3632 (1947) (Abstract).

McKerrow, James H., et al.; "Cysteine Protease Inhibitors as Chemotherapy for Parasitic Infections"; Bioorganic & Medicinal Chemistry 1999 pp. 639-644 vol. 7.

Meirelles, Maria Nazareth L., et al.; Inhibitors of the major cysteinyl proteinase (GP57/51) impair host cell invasion and arrest the intracellular development of *Trypanosoma cruzi* in vitro; Molecular Biochemical Parasitology 1992 pp. 175-184 vol. 52.

Nerurkar et al., "β-arylglutaconic acids. IV. Synthesis of crotono- and valerolactones of β-arylglutaconic and glutaric acids" CAS Accession No. 55:37886 (1961) (Abstract).

Olson, Jed E., et al.; "Antimalarial Effects in Mice of Orally Administered Peptidyl Cysteine Protease Inhibitors"; Bioorganic & Medicinal Chemistry 1999 pp. 633-638 vol. 7.

Otto, Hans-Hartwig, et al.; "Cysteine Proteases and Their Inhibitors"; Chem. Rev. 1997 pp. 133-171 vol. 97.

Palmer, James, T., et al.; "Vinyl Sulfones as Mechanism-Based Cysteine Protease Inhibitors"; J. Med. Chem. 1995 pp. 3193-3196 vol. 38.

Pandeya, S.N., et al.; "Anticonculsant Activity of Thioureido Derivatives of Acetophenone Semicarbazone"; Pharmacological Research 1998 pp. 17-22 vol. 37 No. 1.

Posenthal, Philip, J., et al.; "*Plasmodium falciparum*: Effects of Proteinase Inhibitors on Globin Hydrolysis by Cultured Malaria Parasites"; Experimental Parasitology 1995 pp. 272-281 vol. 80.

Prescott, "Thiosemicarbazones and hydrazonse of α-methylchalcone as potential chemotherapeutic agents" CAS Accession No. 83:126292 (1975) (Abstract).

Ramu, Kumar, et al.; "In Vivo Metabolism and Mass Balance of 4-[4-Fluorophenoxy] Benzaldehyde Semicarbazone in Rats"; Drug Metabolism and Disposition 2000 pp. 1153-1161 vol. 28 No. 10.

Roush, William R., et al.; "Design, Synthesis and Evaluation of D-Homophenylalanyl Epoxysuccinate Inhibitors of the Trypanosomal Cysteine Protease Cruzain"; Tetrahedron 2000 pp. 9747-9762 vol. 56.

Roush, William R., et al.; "Vinyl Sulfonate Esters and Vinyl Sulfonamides: Potent, Irreversible Inhibitors of Cysteine Proteases"; J. Am. Chem. Soc. 1998 pp. 10994-10995 vol. 120.

Saijid, M., et al.; "Cysteine proteases of parasitic organisms"; Molecular & Biochemical Parasitology 2002 pp. 1-21 vol. 120.

Salvati, Luca, et al.; "No donors inhibit *Leishmania infantum* cysteine proteinase activity"; Biochimica et Biophysica Acta 2001 pp. 357-366 vol. 1545.

Sawhney et al., "Synthesis of possible amebicides" CAS Accession No. 54:56188 (1960) (Abstract).

Sawhney et al., "Synthesis of possible amebicides" CAS Accession No. 60:60564 (1964) (Abstract).

Selzer, Paul M., et al.; "Cysteine protease inhibitors as chemotherapy: Lessons from a parasite target"; Proc. Natl. Acad. Sci. 1999 pp. 11015-11022 vol. 96.

Semenov, Andrey, et al.; "Antimalarial Synergy of Cysteine and Aspartic Protease Inhibitors"; Antimicrobial Agents and Chemotherapy 1998 pp. 2254-2258 vol. 42 No. 9.

Sharma et al., "Synthesis of possible amebicides. VII" CAS Accession No. 54:38933 (1960) (Abstract).

Warren, James D., et al.; "4-Substituted Semicarbazones of Mono- and Dichlorobenzaldehydes as Antihypertensive Agents"; Journal of Medicinal Chemistry 1977 pp. 1520-1521 vol. 20 No. 11.

Zsolnai, "Attempts to discover new fungistats. VIII. Antimicrobial activity of new compounds containing an arylazomethylene group" CAS Accession No. 63:83741 (1965) (Abstract).

* cited by examiner

| ID | STRUCTURE | IC50(nm) | ID | STRUCTURE | IC50(nm) |
|---|---|---|---|---|---|
| 4a | 3-Br-phenyl dihydropyrrole thiocarboxamide | 200 | 4e | 3,4-diCl-phenyl dihydropyrrole thiocarboxamide | 60 |
| 4b | 3-Br-phenyl 4-methyl dihydropyrrole thiocarboxamide | 80 | 4f | 3,4-diCl-phenyl 4-methyl dihydropyrrole thiocarboxamide | 70 |
| 4c | 3-Cl-phenyl dihydropyrrole thiocarboxamide | 270 | 4g | 3-CF$_3$-phenyl dihydropyrrole thiocarboxamide | 80 |
| 4d | 3-Cl-phenyl 4-methyl dihydropyrrole thiocarboxamide | 230 | 4h | 3-CF$_3$-phenyl 4-methyl dihydropyrrole thiocarboxamide | 40 |

FIG. 5

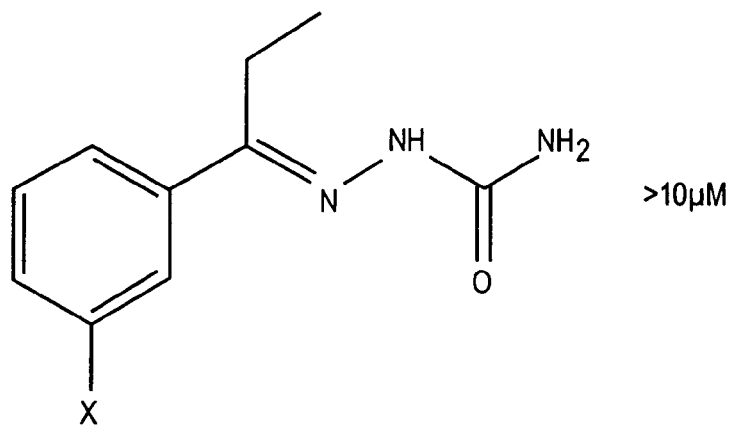
X = Br (6a); CF₃; Cl; 3,4-Cl₂; 3,5-(CF₃)₂   >10µM
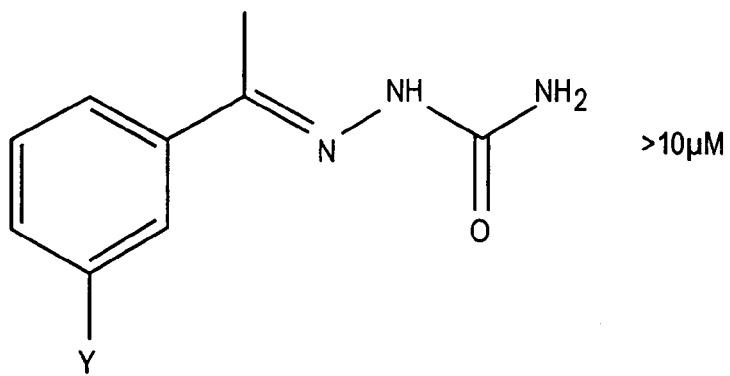
Y = Br (6b); Cl; CF₃; 3,4-Cl₂   >10µM
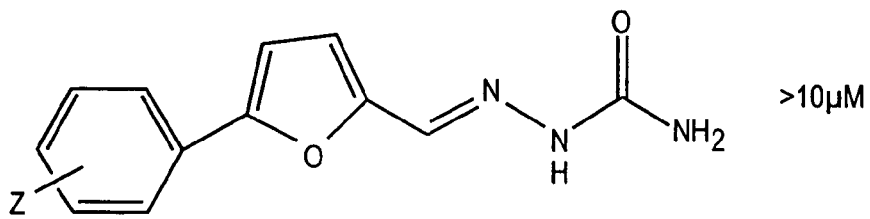
Z = 3-Cl (6c); 4-Cl; 4-Br   >10µM
FIG. 7

| ID | STRUCTURE | DAYS CELL SURVIVED | ID | STRUCTURE | DAYS CELL SURVIVED |
|---|---|---|---|---|---|
| CONTROL | | 5 | | | |
| 1i | 3-bromophenyl ethyl thiosemicarbazone | >46, trypanocidal | 2i | 3,4-dichlorophenyl ethyl thiosemicarbazone | 9, toxic |
| 3b | 3-bromophenyl methyl thiosemicarbazone | >22, trypanocidal | 2h | 3,5-bis(trifluoromethyl)phenyl ethyl thiosemicarbazone | 20, toxic, crystal |
| 3a | 3-bromobenzaldehyde thiosemicarbazone | 8, toxic | 1c | 2-methoxyphenyl furan thiosemicarbazone | 8, toxic |
| 4a | 3-(3-bromophenyl)-4,5-dihydro-1H-pyrazole-1-carbothioamide | 5 | 1b | 4-chlorophenyl furan thiosemicarbazone | 15, crystals |
| 4b | 3-(3-bromophenyl)-4-methyl-4,5-dihydro-1H-pyrazole-1-carbothioamide | >22, trypanocidal | 1n | 2-methoxynaphthyl thiosemicarbazone | 5, toxic |
| 2a | 3-chlorophenyl ethyl thiosemicarbazone | >22, trypanocidal | 5d | 3-(3-bromophenyl)-N-(3-chlorophenyl)-4,5-dihydropyrazole-1-carbothioamide | 5 |
| 5c | 3-bromophenyl ethyl N-(4-trifluoromethylphenyl) thiosemicarbazone | 5 | | | |

FIG. 8

| ID | STRUCTURE | DAYS CELL SURVIVED | ID | STRUCTURE | DAYS CELL SURVIVED |
|---|---|---|---|---|---|
| CONTROL | | 5 | | | |
| 4c | 3-chlorophenyl pyrazoline carbothioamide | 5 | 4e | 3,4-dichlorophenyl pyrazoline carbothioamide | >41, trypanocidal |
| 4g | 3-(trifluoromethyl)phenyl pyrazoline carbothioamide | 5 | 3h | 3,4-dichlorophenyl methyl thiosemicarbazone | >41, trypanocidal |
| 3f | 3,5-bis(trifluoromethyl)phenyl methyl thiosemicarbazone | 7, crystals | 2b | 3-(trifluoromethyl)phenyl ethyl thiosemicarbazone | >41, trypanocidal |
| 3d | 3-(trifluoromethyl)phenyl methyl thiosemicarbazone | 15 | 4d | 4-methyl-3-(3-chlorophenyl) pyrazoline carbothioamide | >41, trypanocidal |
| 4f | 4-methyl-3-(3,4-dichlorophenyl) pyrazoline carbothioamide | 15 | 4h | 4-methyl-3-(3-(trifluoromethyl)phenyl) pyrazoline carbothioamide | >41, trypanocidal |

FIG. 9

The Synthesis of Additional C5-substituted Thio Semicarbazones and Pyrazolines.

FIG. 14 (CONT.)

| Structure | IC50 (nM) | ID |
|---|---|---|
| 3-CF3-phenyl pyrazoline with 4-ethyl, N-C(=S)NH2 | 45 nM | 8k |
| 3-CF3-phenyl pyrazoline with 4-propyl, N-C(=S)NH2 | 55 nM | 8l |
| 3-CF3-phenyl pyrazoline with 4-phenyl, N-C(=S)NH2 | 625 nM | 8m |
| 3-Br-phenyl pyrazoline with 4-benzyl, N-C(=S)NH2 | 420 nM | 8n |

The flexibility of the R2 group, ie., C5 site is consistent with our modeling. R2 might interact with the shallow S1 pocket, therefore any longer group can extend outside of the pocket without influencing the inhibiting activity of the structure. As demonstrated in the above set of compounds, R2 can tolerate a variety of groups with excellent activities. This site can be used for tuning pharmacokinetics as well as for connecting to radiolabels to do further mechanistic study such as with the structures shown below. With the aid of fluorescene or radioactivity, we can detect whether there is covalent inhibitor-cruzain complex existing or not.

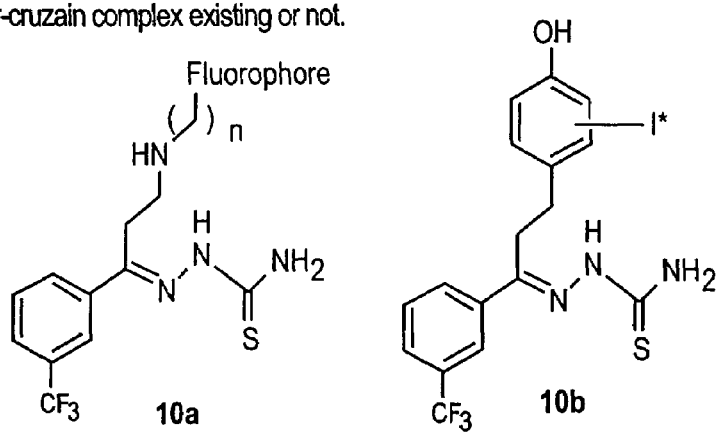

10a (Fluorophore-linked)  10b (with OH and I*)

FIG. 15

In Vitro Data (IC50)

Screener: TIBOTEC

OBJECTIVE: To screen compounds in our integrated in vitro screening system
Activity Criteria:
P.falciparum: IC50<1μM L. infantum: IC50 <4μM T. cruzi: IC50 <4μM  T. brucei: IC50 < 0.25μM T. colubriformis: IC50 < 8μM T. colubriformis legends:
D-1 - Duwel T.cruzi legends:
TC-1 - Tulahuen C4
TC-2-Y/0
TC-3-MHOM BR/00/Y
TC-4- Tulahuen CL2

T. brucei legends:
TB-1 - S427
TB-2 - Lab Estro 110

L. donovani legends:
LD-1 - MHOM-ET-67 L82
LD-2 - HU3

ST1 - Melarsoprol; ST2 - Benzni-dazole; ST3 - Pentostam; ST4 - Chloroquine; ST6 - Mefloquine; ST6 - Quinine; ST7 - Artemeter; ST8 - Nifurtimox
ST9 - ampho B; ST10 - Pentamidine; ST11 - stibogluconate "+" means compound has been tested but activity was not interesting or was inactive

| TDR Number | Supplier No | MW | structure | Tb. bruceiTB-1 μM | Tb. bruceiTB-2 μM | T. cruziTC-1 μM | T. cruziTC-2 μM | T. cruziTC-4 μM | T. colubriformisD-1 μM |
|---|---|---|---|---|---|---|---|---|---|
| ST1 Meier | | 388.34 | | | | | | | |
| ST2 Benz | | 280.25 | | | | | | | |
| ST3 Pento | | 338.88 | | | | | | | |

| | | | | | | | | | |
|---|---|---|---|---|---|---|---|---|---|
| ST4 Chloro | 319.82 | | | | – | – | – | – | |
| ST5 Merto | 442.28 | | | – | – | – | – | – | |
| ST8 Quinine | 324.42 | | | – | – | – | – | – | |
| ST7 Artemeter | 298.38 | | | – | – | – | – | – | |
| ST8 Nifurtimox | 297.3 | | | – | – | 0.43 0.5" | – | – | |
| ST9 ampho-B | 924.09 | | | – | – | – | – | – | |
| ST10 Pents | 340.83 | | | – | – | – | – | – | |
| ST11 stbG | | | – | | | | | – | |
| ST12 Albendazole | | | | | | | | | 0.02 |
| ST13 Suramin | | 0.174 | | | | | | | |
| 13251/1 compound 1I | 286.19 | >32 | | | | 4 5* | | | 32 |

New results *

FIG. 15 (CONT.)

Cytotoxicity: IC50>32μM(non-cytotoxic)

version date: 17/04/2001

L. infantum legends:
L1-1 - MHOM/MA (BE)/67

P. falciparum legends:
D6 / NF54 - sensitive strains
W2 / K - resistant strains

| L. Infantum | | P. falciparum | | Cytoxicity | |
|---|---|---|---|---|---|
| L1 μM | | W2 μM | GHANE μM | L6 μM | MRC-5 μM |
|  |  |  |  |  |  |
|  |  |  |  |  |  |
|  |  |  |  |  |  |
|  |  | 0.085 | 0.0102 |  |  |
| − | − | − | − | − | − |
| − | − | − | − | − | − |
| − | − | − | − | − | − |
|  |  | − | − | − | − |
|  | − | − | − | − | − |
| − | − | − | − | − | − |
| 8 8" | − | − | − | − | − |
|  |  |  |  |  |  |
|  |  |  |  |  |  |
| 10 10" |  | 32 | 16 |  | > 32 |

FIG. 15 (CONT.)

THIO SEMICARBAZONE AND SEMICARBOZONE INHIBITORS OF CYSTEINE PROTEASES AND METHODS OF THEIR USE

CROSS-REFERENCES TO RELATED APPLICATIONS

This application is a continuation of application Ser. No. 10/431,714, filed May 8, 2003, and claims the benefit of U.S. provisional application Ser. No. 60/449,058, filed Feb. 20, 2003; and U.S. provisional application Ser. No. 60/379,366 filed on May 8, 2002; the contents of which are herein incorporated by reference for all purposes.

STATEMENT AS TO RIGHTS TO INVENTIONS MADE UNDER FEDERALLY SPONSORED RESEARCH OR DEVELOPMENT

This invention was made with Government support under Grant Nos. 1F-32-AI10293-02 and AI35707, awarded by the National Institutes of Health. The Government has certain rights in this invention.

BACKGROUND OF THE INVENTION

Trypanosomiasis, malaria, and leishmaniasis are major parasitic diseases in developing countries (McKerrow, J. H. et al., *Annu. Rev. Microbiol.* 47:821-853 (1993)). American trypanosomiasis, or Chagas' disease, is the leading cause of heart disease in Latin America (Libow, L. F. et al., *Cutis,* 48:37-40 (1991)). At least 16-18 million people are infected with *Trypanosoma cruzi*, resulting in more than 50,000 deaths each year (Godal, T. et al., *J. Tropical diseases. WHO Division of Control in Tropical Diseases* World Health Organization: Geneva, Switzerland, pp 12-13. (1990); World Health Organization website: http://www.who.int/ctd/html/chagburtre.html). The statistics for malaria are more sobering, with about 300-500 million clinical cases and about 3 million deaths each year. Further, at least 10 million people are infected with a form of *Leishmania* each year (see *Goodman & Gilman's The Pharmacological Basis of Therapeutics,* 9th Ed, 1996, McGraw-Hill, New York).

Chagas' disease is transmitted to humans by blood-sucking triatomine vectors with an infectious trypomastigote form of the protozoan parasite *T. cruzi* (Bonaldo, M. C. et al., *Exp. Parasitol,* 73:44-51 (1981); Harth, G., et al., *T. Cruzi. Mol. Biochem Parasitol,* 58:17-24 (1993); Meirelles, M. N. L., et al., *Mol. Biochem. Parasitol,* 52:175-184 (1992)). African trypanosomiasis is transmitted to humans and cattle by tsetse flies and is caused by subspecies of *T. brucei*. So called "African sleeping sickness" is transmitted by an infectious trypomastigote from *T. brucei gambiense*, and *T. brucei rhodesiense* produces a progressive and usually fatal form of disease marked by early involvement of the central nervous system. *T. brucei* is further the cause of nagana in cattle, but bovine trypanosomiasis is also transmitted by *T. congolense* and *T. evansi*. In trypanosomiasis infections, the trypomastigote enters the host bloodstream and ultimately invades a cardiac muscle cell, where it transforms into the intracellular amastigote. The parasite may also be found in the blood, lymph, spinal fluid and cells of the gastrointestinal tract. Amastigotes replicate within cells, transform back to trypomastigotes, and rupture the cell, releasing the infectious form back into the bloodstream and other cells, amplifying the infection. Reviews of the current understanding and treatment of African and American trypanosomiasis infections is provided by Urbina (*Curr Pharm Des* (2002) 8:287) and Burchmore, et al (*Curr Pharm Des* (2002) 8:256).

Cruzain (aka cruzipain) is the major cysteine protease of *T. cruzi*. The protease is expressed in all life cycle stages of the parasite, but delivered to different cellular compartments in each stage. In the epimastigote stage, which occurs in the insect vector, the protease is in a lysosomal compartment where it functions to degrade proteins endocystosed from the insect gut. In the infectious trypomastigote stage, the protease appears at the flagellar pocket, the site of endocytosis and secretion. In the amastigote stage, within the mammalian host cell, the protease is both in the lysosomal compartment and on the surface of the parasite where it may function in nutrition, remodeling of the mammalian cell, or evasion of host defense mechanisms. Addition of a cruzain inhibitor such as Z-Phe-Ala-FMK (benzyloxy-carbonyl-L-phenylalanyl L-alanine fluoromethyl ketone) to cultures of mammalian cells exposed to trypomastigotes or to mammalian cells already infected with *T. cruzi* amastigotes blocks replication and differentiation of the parasite (Bonaldo, M. C. et al., *Exp. Parasitol,* 73:44-51 (1981); Harth, G., et al., *T. Cruzi Mol. Biochem Parasitol,* 58:17-24 (1993); Meirelles, M. N. L., et al., *Mol. Biochem. Parasitol,* 52:175-184 (1992)), thus arresting the parasite life cycle. Therefore, cruzain is essential for replication of the intracellular parasite. Treatment of *T. cruzi*-infected mice with a vinyl sulfone-derivatized pseudopeptide inhibitor of cruzain, N-methyl piperazine-Phe-homoPhe-vinyl sulfone phenyl, has resulted in a cure in a mouse model study (Engel, J. C. et al., *J. Exp. Med.,* 188:725-734 (1998)). Thus, cruzain is an appealing target for new antitrypanosomal chemotherapy (McKerrow, J. H. et al., *Bioorg. Med. Chem.,* 7:639-644 (1999)).

Malaria is caused by protozoa of the genus *Plasmodium* and is transmitted to humans through the bite of an infected anopheline mosquito. The parasites develop into tissue schizonts in hepatic parenchymal cells, and then are released into the circulation as merozoites, which invade erythrocytes. In erythrocytes, the merozoites mature from trophozoites into schizonts. Schizont-containing erythrocytes rupture to release merozoites that then invade more erythrocytes to continue the malarial cycle. Current understanding and treatment of *plasmodium* infections is reviewed in Winstanley (*Lancet Infect Dis* (2001) 1:206), Wongsrichanalai, et al (*Lancet Infect Dis* (2002) 2:209) and throughout the Feb. 7, 2002 issue of *Nature* (*Lond*) (vol. 415, issue 6872).

The majority of malaria infections is caused by *Plasmodium falciparum* (see *Goodman & Gilman's The Pharmacological Basis of Therapeutics,* supra). Papain-family cysteine proteases, known as falcipains, are hemoglobinases from *P. falciparum* that are essential to *plasmodium* trophozoite protein synthesis and development (Sijwali, et al (2001) *Biochem J* 360:481). Sequencing of the *Plasmodium* genome has revealed at least three falcipain cysteine proteases, designated falcipain-1, falcipain-2 and falcipain-3, where falcipain-2 and falcipain-3 are understood to account for the majority of hemoglobinase activity in the *plasmodium* trophozoite (Joachimiak, et al (2001) *Mol. Med* 7:698). The falcipains are homologous to cruzain (Venturini, et al (2000) *Biochem Biophys Res Commun* 270:437 and Selzer, et al (1997) *Exp Parasitol* 87:212) and at least the falcipain-2 sequence is highly conserved amongst different *Plasmodium* strains with different sensitivities to established antimalarial drugs (Singh and Rosenthal (2001) *Antimicrob Agents Chemother* 45:949). In in vitro studies, cysteine protease inhibitors blocked globin hydrolysis in *Plasmodium* infected erythrocytes (Rosenthal (1995) *Exp. Parasitol* 80:272 and Semenov et al (1998) *Antimicrob Agents Chemother* 42:2254). Importantly, oral or parenteral administration of fluoromethyl ketone or vinyl sulfone peptidyl inhibitors of falcipain cured treated mice that were infected with *Plasmodium* (Olson, et al (1999) *Bioorg Med Chem* 7:633). Therefore, the falcipains and other homologous cysteine proteases are also important antimalarial chemotherapeutic targets.

Leishmaniasis is caused by protozoal species and subspecies of *Leishmania* transmitted to humans by the bites of infected female phlebotamine sandflies. Promastigotes injected into the host are phagocytized by tissue monocytes and are transformed into amastigotes, which reside in intracellular phagolysosomes. Human leishmaniasis is classified into cutaneous, mucocutaneous and visceral (kala azar) forms. Reviews of the current understanding and chemotherapy of leishmaniasis is provided by Croft and Yardley (*Curr Pharm Des* (2002) 8:319), Kafetzis, et al (*Curr Opin Infect Dis* (2002) 15:289, and Hepburn (*Curr Opin Infect Dis* 14:151).

In vitro and in vivo studies also have demonstrated that cysteine protease inhibitors disrupt the infectious life cycle of *Leishmania* (see, Selzer, et al (1999) *Proc Natl Acad Sci* 96:11015; Das, et al (2001) *J. Immunol* 166:4020 and Salvati, et al (2001) *Biochim Biophys Acta* 1545:357). Like *Trypanosoma* and *Plasmodium*, *Leishmania* synthesize cathepsin-L-like cysteine proteases that are essential to their pathogenicity (Selzer, et al (1997) *Exp Parasitol* 87:212). The substrate recognition of one cysteine protease of *L. mexicana*, named CPB2.8 Delta CTE, has been demonstrated to be similar to the substrate preferences of cruzain (Alves, et al (2001) *Mol Biochem Parasitol* 117:137 and Alves, et al (2001) *Mol Biochem Parasitol* 116:1). Additionally, cruzain shares sequence similarity with homologous cysteine proteases from *L. pifanoi, L. mexicana,* and *L. major* (see Mottram, et al (1992) *Mol Microbiol* 6:1925, Rafati, et al (2001) *Mol Biochem Parasitol* 113:35 and GenBank numbers L29168, X62163 and AJ130942). Therefore, cysteine proteases also represent a potential chemotherapeutic target against *Leishmania* infections.

Drugs currently used in the treatment of trypanosomiasis include Nifurtimox, Benznidazole, Suramin, Pentamidine isethionate, Eflornithine and Melarsoprol. Current chemotherapeutics for the treatment of leishmaniasis include Stibogluconate sodium, Amphotericin B, and Pentamidine isethionate. Drugs used in the treatment of malaria include chloroquine phosphate, mefloquine, halofantrine, and quinidine gluconate in combination with an antifolate or an antibiotic. Although these protozoans are inhibited to some extent by the administration of available chemotherapeutics, the currently prescribed pharmacological compounds to counteract trypanosomiasis, malaria, and leishmaniasis are limited by the ability of the parasites to develop resistance to them and by their significant toxicity to the infected host. Therefore, there is an interest in developing new drugs that will interfere with the infectious life cycle of a parasite. Because cysteine proteases are essential to the life cycle of the parasites that cause trypanosomiasis, malaria and leishmaniasis, they are a logical target for newly developed chemotherapeutics (reviewed in Sajid and McKerrow, *Mol Biochem Parasitol* (2002) 120:1).

Several irreversible peptide-based inhibitor series including halomethyl ketones, diazomethanes, epoxysuccinyl derivatives, and vinyl sulfone derivatives targeting cysteine proteases have been developed (Otto, H. et al., *Chem. Rev.*, 97:133-171 (1997)). A disadvantage of the chloromethyl ketones is their high reactivity and consequent lack of selectivity. They react with serine proteases and other SH-containing molecules, such as glutathione or nonproteolytic enzymes, and result in toxicity in vivo. To increase selectivity and reduce reactivity and toxicity, a less reactive series of compounds, including monofluoro methyl ketones, epoxy derivatives (Roush, W. R. et al., *Tetrahedron*, 56:9747-9762 (2000)), and vinyl sulfone derivatives (Bromme, D. et al., *Biochem. J.*, 315:85-89 (1996); Palmer, J. T. et al., *J. Med Chem.* 38:3193-3196 (1995); Roush, W. R. et al., *J. Am. Chem. Soc.* 120:10994-10995 (1998)) were developed. However, the low oral bioavailability associated with peptidyl inhibitors makes the further pursuit of effective chemical compounds of great interest.

Pharmaceutical compounds having a semicarbazone scaffold have been evaluated for clinical use as an antihypertensive (Warren, J. D. et al., J. Med. Chem., 20:1520-1521 (1977)), anticonvulsant (Dimmock, J. R. et al., Epilepsia, 35:648-655 (1994); Pandeya, S. N. et al., Pharmacol Res., 37:17-22 (1998); Dimmock, J. R. et al., Drug Dev Res., 46:112-125 (1999)), and antiallodynic agent (Carter, R. B. et al., Proceeding, International Symposium "Ion Channels in Pain and Neuroprotection" March 14-17, San Francisco, Calif.; p 19 (1999)). For example, the semicarbazone compound 4-[4-fluorophenoxy]benzaldehyde semicarbazone has entered clinical trials for the treatment of neuropathic pain (Ramu, K. et al., Drug Metab. Dispos., 28:1153-1161 (2000)). Recently, 5-nitrofurfural N-butyl semicarbazone (Cerecetto. H. et al., Farmaco, 53:89-94 (1998); Cerecetto, H. et al., J. Med. Chem., 42:1941-1950 (1999); Cerecetto, H. et al., Eur. J. Med. Chem., 35:343-350 (2000)) has been shown to have antitrypanosomal activities targeting trypanothione reductase through a nitro anion radical mechanism, however, no clear target validation was reported in these papers.

Therefore, there is a pressing interest in developing potent, efficacious, economically synthesized pharmaceutical compounds with minimal toxicity and maximal bioavailability for the effective treatment of these infectious parasitic diseases.

SUMMARY OF THE INVENTION

The present invention relates to thio semicarbazone and semicarbazone compounds, and cyclized pyrazoline analogues of either, that function as cysteine protease inhibitors and the use of such compounds in methods of treating and preventing protozoan infections that require cysteine protease activity for their infectious lifecycle. The compounds also find use in inhibiting cysteine proteases associated with malignancy of cancer cells.

In one aspect, the present invention relates to a method for inhibiting a cysteine protease involved in the infectious life cycle of a protozoan parasite, the method comprising the step of administering to the subject a pharmaceutical composition comprising a pharmaceutically acceptable carrier and a compound that inhibits such a cysteine protease, said composition administered to the subject in an amount sufficient to inhibit the target cysteine protease and disrupt the infectious life cycle of a protozoan parasite, wherein the compound forms a reversible covalent association with a cysteine in the active site of the target cysteine protease.

In another aspect the present invention relates to a method for treating or preventing a protozoan parasitic disease or infection, the method comprising the step of administering to the subject a pharmaceutical composition comprising a pharmaceutically acceptable carrier and a compound that inhibits a cysteine protease required in the infectious life cycle of the protozoan parasite, said composition administered to the subject in an amount sufficient to inhibit the target cysteine protease and disrupt the infectious life cycle of a protozoan parasite thereby treating or preventing a protozoan parasitic disease or infection in the subject.

Exemplary protozoan cysteine proteases include those required in the infectious life cycle of a trypanosome, such as cruzain or cruzipain from *T. cruzi*, rhodesain or brucipain from *T. brucei rhodesiense*, and congopain from *T. congolense*; a *plasmodium*, such as falcipain from *P. falciparum*; or a *leishmania*, such as CPB2.8 Delta CTE from *L. mexicana*.

In one embodiment, the cysteine protease is a cathepsin L-like protease.

In one embodiment, the cysteine protease is a cathepsin B-like protease.

In one embodiment, the protozoan parasite is a *Trypanosoma*, a *Plasmodium* or a *Leishmania*.

In a further embodiment, the parasite is selected from the group consisting of *Trypanosoma cruzi, Trypanosoma brucei gambiense, Trypanosoma brucei rhodesiense, Trypanosoma rangeli, Trypanosoma congolense, Plasmodium falciparum, Plasmodium malariae, Plasmodium vivax, Plasmodium ovale, Leishmania major, Leishmania braziliensis, Leishmania mexicana, Leishmania donvani, Leishmania pifanoi* and *Leishmania tropica*.

In one embodiment the parasitic disease is selected from the group consisting of Chagas' disease, African sleeping sickness, nagana, malaria, and leishmaniasis (cutaneous, mucocutaneous or visceral).

In one aspect, the invention relates to a method of inhibiting a mammalian cysteine protease involved in the malignancy of a cancer cell, the method comprising the step of administering to an individual in need thereof a composition comprising a pharmaceutically acceptable carrier and a compound that inhibits the mammalian cysteine protease by forming a reversible covalent association with a cysteine in the active site of the target cysteine protease.

In one embodiment, the cancer a breast cancer, an oral cancer, a skin cancer, a lung cancer, an intestinal cancer, a bladder cancer or a prostate cancer. In a further embodiment, the cancer is a breast carcinoma, an oral squamous cell carcinoma, a melanoma, a transitional cell carcinoma of the bladder, an intestinal adenoma, a colorectal carcinoma, a neuroblastoma or a prostate carcinoma. In another embodiment, the cancer is a metastatic cancer.

In another aspect, the invention relates to a method of inhibiting a mammalian cysteine protease involved in an inflammatory disease, the method comprising the step of administering to an individual in need thereof a composition comprising a pharmaceutically acceptable carrier and a compound that inhibits the mammalian cysteine protease by forming a reversible covalent association with a cysteine in the active site of the target cysteine protease.

In one embodiment the inflammatory disease is rheumatoid arthritis, atherosclerosis, vascular inflammation, allergic lung inflammation or multiple organ failure.

In one embodiment, the mammalian cysteine protease is a cathepsin L, a cathepsin B, a cathepsin H or a cathepsin K.

In one embodiment, the subject or individual is a mammal. In a further embodiment, the mammal is human, primate, canine, feline, equine, bovine, ovine, porcine, murine or lagomorpha.

The compounds are exemplified by a structural scaffold of the chemical formula:

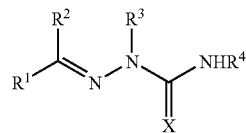

wherein $R^1$ is a member selected from the group consisting of substituted or unsubstituted aryl and substituted or unsubstituted heteroaryl;

$R^2$ is substituted or unsubstituted alkyl, allyl, and alkyl substituted with aryl;

$R^3$ is a member selected from the group consisting of H, and substituted or unsubstituted lower alkyl, and $R^2$ and $R^3$ are optionally joined to form a ring system having the formula:

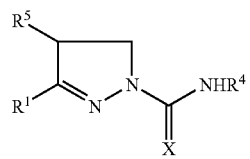

$R^4$ is a member selected from H, alkyl substituted with saturated rings, aryl, or unsubstituted lower alkyl;

$R^5$ is a member selected from the group consisting of H, aryl, and substituted or unsubstituted alkyl; and X is O or S. Preferably, the compounds inhibit a target cysteine protease of interest with a potency or IC50 value of less than 1000 nanomolar (nM), more preferably of less than about 500, 300 or 100 nM, and most preferably less than about 80, 70, 60, 50, 40, 30, 20, or 10 nM.

In one embodiment, $R^1$ is a member selected from the group consisting of:

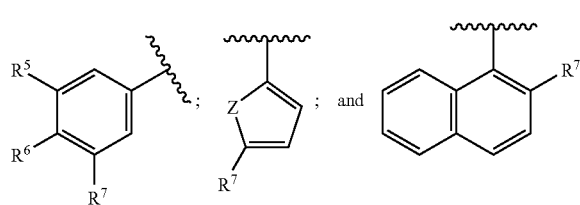

wherein $R^5$, $R^6$, and $R^7$ are members independently selected from the group consisting of H, substituted or unsubstituted alkyl, substituted or unsubstituted aryl, substituted or unsubstituted heteroaryl, haloalkyl, alkoxy and halo; and Z is S or O.

In a further embodiment, $R^1$ is:

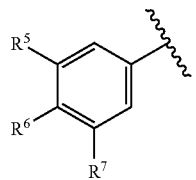

wherein $R^5$, $R^6$ and $R^7$ are members independently selected from H, halo and haloalkyl.

In a further embodiment, $R^5$ is H or haloalkyl; $R^6$ is H or halo; and $R^7$ is halo or $CF_3$.

In one embodiment, $R^2$ is a member selected from the group consisting of H, $CH_3$, and $CH_2CH_3$.

In one embodiment, $R^5$ is a member selected from the group consisting of H, $CH_3$, and $CH_2CH_3$.

In one aspect, the compounds are provided as part of a pharmaceutical composition. An exemplified pharmaceutical composition includes at least one compound such as a thio semicarbazone, a semicarbazone or a cyclized pyrazoline analogue of either, in a pharmaceutically acceptable carrier, such that administration of the composition to an individual would render the one or more compounds sufficiently bioavailable to effectively inhibit a target cysteine protease.

In one embodiment, the one or more compounds inhibit a target cysteine protease without inducing toxicity in a host cell or host tissue infected with a protozoan whose infectious life cycle requires the activity of the target protease or in a non-malignant host cell or host tissue that does not express a cysteine protease associated with a malignant cancer cell. Generally, the compounds form a reversible covalent interaction with a cysteine in the active site of a target cysteine protease as part of their inhibitory mechanism.

In one embodiment, the compounds are at least one of *Trypanocidal*, *Plasmodium*-cidal, and *Leishmania*-cidal.

In one embodiment, the compounds are at least one of *Trypanostatic*, *Plasmodium*-static, and *Leishmania*-static.

Exemplary compounds, which find particular use in a pharmaceutical composition of the invention, include:
a) 3'-Bromopropiophenone Thio Semicarbazone (1i),
b) 3'-Chloropropiophenone Thio Semicarbazone (2a),
c) 3'-Trifluoromethylpropiophenone Thio Semicarbazone (2b),
d) 3'-Bromoacetophenone Thio Semicarbazone (3b),
e) 3,4-Dichlorobenzaldehyde Thio Semicarbazone (3g)
f) 3',4'-Dichloroacetophenone Thio Semicarbazone (3h),
g) 3-(3-Bromophenyl)-4-methyl-2-pyrazoline-1-thiocarboxamide (4b),
h) 3-(3-Chlorophenyl)-4-methyl-2-pyrazoline-1-thiocarboxamide (4d),
i) 3-(3,4-Dichlorophenyl)-2-pyrazoline-1-thiocarboxamide (4e),
j) 3-(3-Trifluoromethylphenyl)-4-methyl-2-pyrazoline-1-thiocarboxamide (4h),
k) 3',5'-bis(trifluoromethyl)propiophenone Thio Semicarbazone (2h),
l) 3',4'-Dichloropropiophenone Thio Semicarbazone (2i),
m) 3-Trifluoromethylacetophenone Thio Semicarbazone (3d),
n) 3',5'-Bis(trifluoromethyl)acetophenone Thio Semicarbazone (3f),
o) 3-(3,4-Dichlorophenyl)-4-methyl-2-pyrazoline-1-thiocarboxamide (4f), and
p) 3-(3-Trifluoromethylphenyl)-2-pyrazoline-1-thiocarboxamide (4g).

Compounds of further interest include:
4-(Phenylethynyl)thiophene-2-carboxyaldehyde Thio Semicarbazone (1a),
5-(4-Chlorophenyl)-2-furancarboxaldehyde Thio Semicarbazone (1b),
5-(2-Methoxyphenyl)-2-furancarboxaldehyde Thio Semicarbazone (1c),
2-(1-Methyl-3-trifluoromethyl)pyrazol-5-yl)-thiophene-5-carboxaldehyde Thio Semicarbazone (1d),
5-(3-Chlorophenyl)-2-furancarboxaldehyde Thio Semicarbazone (1e),
5-(4-Bromophenyl)-2-furancarboxaldehyde Thio Semicarbazone (1f),
1-(Phenylsulfonyl)-2-pyrrolecarboxaldehyde Thio Semicarbazone (1g),
4'-Morpholinoacetophenone Thio Semicarbazone (1h),
3-Hydroxy-4-methoxybenzaldehyde Thio Semicarbazone (1j),
6'-Methoxy-2'-propiononaphthone Thio Semicarbazone (1k),
4-Dimethylamino-1-naphthaldehyde Thio Semicarbazone (1l),
1-Methylindole-3-carboxaldehyde Thio Semicarbazone (1m),
2-Methoxy-1-naphthaldehyde Thio Semicarbazone (1n),
3'-Fluoropropiophenone Thio Semicarbazone (2c),
Propiophenone Thio Semicarbazone (2d),
4'-Bromopropiophenone Thio Semicarbazone (2e),
4'-Chloropropiophenone Thio Semicarbazone (2f),
4'-Methoxypropiophenone Thio Semicarbazone (2g),
2',4'-Dichloropropiophenone Thio Semicarbazone (2j),
3'-Methoxyacetophenone Thio Semicarbazone (2k),
2'-Bromoacetophenone Thio Semicarbazone (2l),
2'-Chloroacetophenone Thio Semicarbazone (2m),
2,3-Dichlorobenzaldehyde Thio Semicarbazone (2n),
3,5-Dichlorobenzaldehyde Thio Semicarbazone (2o),
2-Trifluoromethylbenzaldehyde Thio Semicarbazone (2p),
3-Bromobenzaldehyde Thio Semicarbazone (3a),
3-Trifluoromethylbenzaldehyde Thio Semicarbazone (3c),
3,5-Bis(trifluoromethyl)benzaldehyde Thio Semicarbazone (3e),
2-Acetyl-5-bromothiophene Thio Semicarbazone (3i),
2-Acetyl-5-chlorothiophene Thio Semicarbazone (3j),
3-(3-Bromophenyl)-2-pyrazoline-1-thiocarboxamide (4a),
3-(3-Chlorophenyl)-2-pyrazoline-1-thiocarboxamide (4c),
3'-Bromopropiophenone N-Methyl Thio Semicarbazone (5a),
3-(3-Bromophenyl)-2-pyrazoline-1-(N-methyl)thiocarboxamide (5b),
3'-Bromopropiophenone N-(4-Trifluoromethylphenyl) Thio Semicarbazone (5c),
3-(3-Bromophenyl)-2-pyrazoline-1-(IL3-chlorophenyl)thiocarboxamide (5d),
3-(3-Chlorophenyl)-2-pyrazoline-1-(N-3-tri-fluoromethylphenyl)thiocarboxamide (5e),
3-(3-Bromophenyl)-2-pyrazoline-1-(N-hexyl)-thiocarboxamide (5f),
3'-Bromopropiophenone Semicarbazone (6a),
3'-Bromoacetophenone Semicarbazone (6b) and
5-(3-Chlorophenyl)-2-furancarboxaldehyde Semicarbazone (6c)
3'-Bromobutyrophenone thio Semicarbazone (8a)

3'-Bromovalerophenone thio Semicarbazone (8b)
1-(3'-Bromophenyl)-3-butenone thio Semicarbazone (8c)
1-(3'-Bromophenyl)-2-phenylethanone thio Semicarbazone (8d)
1-(3'-Bromophenyl)-3-phenylpropanone thio Semicarbazone (8e)
3'-trifluoromethylbutyrophenone thio Semicarbazone (8f)
3'-trifluoromethylvalerophenone thio Semicarbazone (8g)
1-(3'-trifluoromethyl)-3-butenone thio Semicarbazone (8h)
1-(3'-trifluoromethyl)-2-phenylethanone thio Semicarbazone (8i)
1-(3'-trifluoromethyl)-3-phenylpropanone thio Semicarbazone (8j)
3-(3-trifluoromethylphenyl)-4-ethyl-2-pyrazoline-1-Thiocarboxamide (8k)
3-(3-trifluoromethylphenyl)-4-propyl-2-pyrazoline-1-Thiocarboxamide (8l)
3-(3-trifluoromethylphenyl)-4-phenyl-2-pyrazoline-1-Thiocarboxamide (8m)
3-(3-bromophenyl)-4-benzyl-2-pyrazoline-1-Thiocarboxamide (8n)

BRIEF DESCRIPTION OF THE DRAWINGS

FIG. 5 shows that cyclized pyrazoline analogues are generally potent inhibitors of cruzain. Compounds in bold have lower (better) IC50 values than compound 1i.

FIG. 7 shows that semicarbazone analogues of the most potent thio semicarbazones poorly inhibit cruzain, as indicated by the high IC50 values.

FIG. 8 shows the cell culture activity of representative thio semicarbazones.

FIG. 9 shows the cell culture activity of additional thio semicarbazone compounds with low IC50 values.

FIG. 15 shows in vitro data and IC50s for compounds.

DETAILED DESCRIPTION OF THE INVENTION

Introduction

Figure 1:
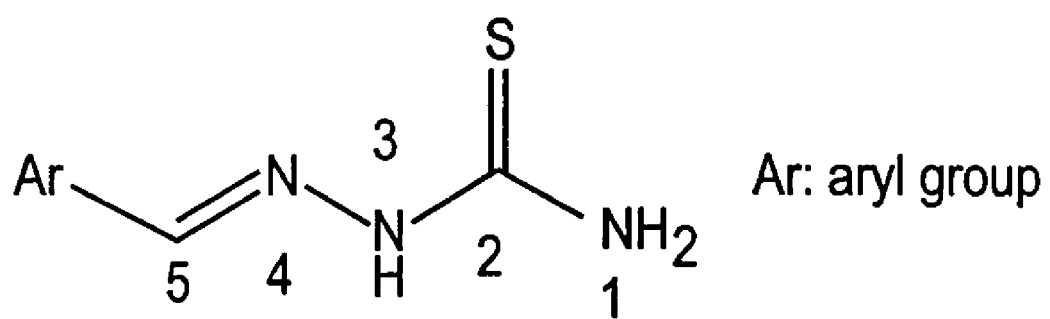
FIG. 1 shows a thio semicarbazone scaffold.

*Trypanosoma*, *Leishmania* and *Plasmodium* infections require the action of a parasitic cysteine protease to complete their infectious life cycle. In this application, we report that thio semicarbazones and related analogues represent a novel series of small-molecule compounds that disrupt the parasitic infectious life cycle through inhibition of essential cysteine proteases and serve as promising agents for antiparasitic therapy. These inhibitors of cysteine proteases, including cathepsin-L like cysteine proteases, have specific structure activity relationships which will allow for the development of additional potent inhibitors of cysteine proteases involved in parasitic disease states such as malaria, leishmaniasis and trypanosomiasis (e.g., Chagas' disease). The advantages of the compounds are many, including (i) minimal cellular toxicity, (ii) physical properties compatible with desirable pharmacokinetics (low molecular weight, favorable C log P, favorable hydrogen bond donating and accepting capabilities), (iii) high potency of target inhibition, with $IC_{50}$ values at the low nanomolar level, (iv) parasiticidal and parasitistatic efficacy against parasite infections of cells, (v) efficient synthesis and inexpensive production, and (vi) improved bioavailability over peptidyl inhibitors. The parasiticidal activity of the thio semicarbazones represents a significant advance. For example, the most potent and efficacious acylhydrazide- and urea-based cathepsin-L like inhibitors are only trypanostatic for 18 and 22 days, respectively.

Thio semicarbazone compounds also find use in the inhibition of related mammalian cysteine proteases, including cathepsin L, cathepsin B, cathepsin H, cathepsin K and cathepsin S. The catalytic activities of these cysteine proteases have been implicated in the pathogenesis of cancer and inflammation (reviewed in Banks, et al, *Adv Exp Med Biol* (2000) 477:349 and Dickenson *Crit Rev Oral Biol Med* (2002) 13:238). For example, cathepsin L, cathepsin B and cathepsin H are used as correlative prognostic indicators of the increased invasiveness, malignancy and growth status of numerous cancers including breast carcinoma, oral squamous cell carcinoma, melanoma, transitional cell carcinoma of the bladder, intestinal adenoma, colorectal carcinoma, neuroblastoma and prostate carcinoma (see, for example, Kawasaki, et al, *Oral Surg Oral Med Oral Pathol Oral Radiol Endod* (2002) 93:446; Staack, et al, *Urology* (2002) 59:308; Levicar, et al, *Cancer Detect Prev* (2002) 26:42; Marten, et al, *Gastroenterology* (2002) 122:406; Jagoe, et al, *Clin Sci (Lond)* (2002) 102:353; Sinha, et al, *Cancer* (2002) 94:3141; Castino, et al, *Int J Cancer* (2002) 97:775; Waghray, et al, *J Biol Chem* (2002) 277:11533; Murnane, et al, *Cancer Res* (1991) 51:1137; Shuja, et al, *Int J Cancer* (1991) 49:341; Foekens, et al, *J Clin Oncol* (1998) 16:1013; Friedrich, et al, *Eur J Cancer* (1999) 35:138; Kos, et al, *Clin Cancer Res* (1997) 3:1815; and Strojan, et al, *Clin Cancer Res* (2000) 6:1052). Additionally, mRNA and protein expression of cathepsin K, a likely contributor to bone metastasis in breast cancer, has been observed in breast cancer cells (Ishikawa, et al, *Mol Carcinog* (2001) 32:84). With regard to inflammatory conditions, the catalytic action of cathepsin B has been associated with rheumatoid arthritis, atherosclerotic plaque rupture and vascular inflammation, T cell migration in allergic lung inflammation, and as a contributing protease to multiple organ failure (see, Zwicky, et al, *Biochem J* (2002) 367:209-217; Chen, et al, *Circulation* (2002) 105:2766; Layton, et al, *Inflamm Res* (2001) 50:400; and Jochum, et al, *Am J Respir Crit Care Med* (1994) 150:S 123). Additionally, chronic inflammation and extracellular matrix degradation preliminary to abdominal aortic aneurysm is associated with a 30-fold increased transcriptional expression of cathepsin H (Tung, et al, *J Vasc Surg* (2001) 34:143). Numerous studies have demonstrated the efficacy of inhibiting cathepsin L or cathepsin B in counteracting pathogenic processes of cancer and inflammation (see, for example, Katunuma, et al, *Arch Biochem Biophys* (2002) 397:305; Katunuma, et al, *Adv Enzyme Regul* (2002) 42:159; Greenspan, et al, *J Med Chem* (2001) 44:4524; Kobayashi, et al, *Cancer Res* (1992) 52:3610; Kolkhorst, V, et al, *J Cancer Res Clin Oncol* (1998) 124:598; Krueger, et al, *Cancer Res* (1999) 59:6010; Sexton and Cox, *Melanoma Res* (1997) 7:97; Cox, et al, *Melanoma Res* (1999) 9:369; Castino, et al, supra; and Layton, et al, supra).

Definitions

The terms "cysteine protease" or "cysteine proteinase" or "cysteine peptidase" intend any enzyme of the sub-subclass EC 3.4.22, which consists of proteinases characterized by having a cysteine residue at the active site and by being irreversibly inhibited by sulfhydryl reagents such as iodoacetate. Mechanistically, in catalyzing the cleavage of a peptide amide bond, cysteine proteases form a covalent intermediate, called an acyl enzyme, that involves a cysteine and a histidine residue in the active site (Cys25 and His159 according to papain numbering, for example). Cysteine protease targets of particular interest in the present invention belong to the family C1 within the papain-like clan CA. Representative cysteine protease targets for the present invention include papain, cathepsin B (EC 3.4.22.1), cathepsin H (EC 3.4.22.16), cathepsin L (EC 3.4.22.15), cathepsin K, cathepsin S (EC 3.4.22.27), cruzain or cruzipain, rhodesain, brucipain, congopain, falcipain and CPB2.8 Delta CTE. Preferred cysteine protease targets of the present invention cleave substrate amino acid sequences -Phe-Arg-|-Xaa-, -Arg-Arg-|-Xaa-, -Val-Val-Arg-|-Xaa- or -Gly-Pro-Arg-|-Xaa-. Clan CA proteases are characterized by their sensitivity to the general cysteine protease inhibitor, E64 (L-trans-epoxysuccinyl-leucyl-amido (4-guanidino)butane) and by having substrate specificity defined by the $S_2$ pocket.

Cysteine proteases of the present invention can be "cathepsin L-like" or "cathepsin B-like." A cathepsin L-like cysteine protease shares structural and functional similarity with a mammalian cathepsin L, and comprises a "ERFNIN" motif (Sajid and McKerrow, supra). Cathepsin L-like cysteine proteases prefer as a substrate the dipeptide sequence -Phe-Arg-|-Xaa-. Representative cathepsin L-like cysteine proteases include cathepsin L, cathepsin K, cathepsin S, cruzain, rhodesain and congopain, *T. cruzi*-L, *T. rangeli*-L, *T. congolense*-L, *T. brucei*-L, *P. falciparum*-L1, *P. falciparum*-L2, *P. falciparum*-L3, *P. vivax*-L1, *P. cynomolgi*-L1, *P. vinckei*-L and *L. major*-L. A cathepsin B-like cysteine protease shares structural and functional similarity with a mammalian cathepsin B, and comprises an "occluding loop" (Sajid and McKerrow, supra). Cathepsin B-like cysteine proteases cleave as a substrate the dipeptide sequences -Arg-Arg-|-Xaa- and -Phe-Arg-|-Xaa-. Representative cathepsin B-like proteases include cathepsin B, *T. cruzi*-B, *L. mexicana*-B and *L. major*-B.

"Inhibitors" or "inhibition" of cysteine proteases refers to inhibitory compounds identified using in vitro and in vivo assays for cysteine protease function. In particular, inhibitors refer to compounds that decrease or obliterate the catalytic function of the target cysteine protease, thereby interfering with or preventing the infectious life cycle of a parasite or the migratory capacity of a cancer cell or an inflammatory cell. In vitro assays evaluate the capacity of a compound to inhibit the ability of a target cysteine to catalyze the cleavage of a test substrate. Cellular assays evaluate the ability of a compound to interfere with the infectious life cycle of a parasite or the migration of a cancer or inflammatory cell ex vivo, while not exhibiting toxicity against the host cell. Cellular assays measure the survival of a parasite-infected cell in culture. Preferred inhibitors allow for extended survival of an infected cell, either by delaying the life cycle of the parasite, or by killing the parasite. In vivo assays evaluate the efficacy of test compounds to prevent or ameliorate disease symptoms, such as those associated with parasitic infection, cancer invasion or growth, or inflammatory cell migration. Inhibitors are compounds that eliminate or diminish the catalytic function of a cysteine protease. Further, preferred inhibitors delay, interfere with, prevent or eliminate the completion of the infectious life cycle of a parasite or the migratory ability of a cancer cell or an inflammation cell. Additionally, preferred inhibitors prevent or diminish a parasitic infection in an individual or the migration of cancer cells or inflammatory cells in an individual, thereby preventing or ameliorating the pathogenic symptoms associated with such infections or the migration of rogue cells.

To examine the extent of inhibition, samples, assays, cultures or test subjects comprising a target cysteine protease are treated with a potential inhibitor compound and are compared to negative control samples without the test compound, and positive control samples, treated with a compound known to inhibit the target cystein protease. Negative control samples (not treated with a test compound), are assigned a relative cysteine protease activity level of 100%. Inhibition of a cysteine protease is achieved when the cysteine protease activity relative to the control is about 90%, preferably 75% or 50%, more preferably 25-0%.

An amount of compound that inhibits a cysteine protease, as described above, is "an amount sufficient to inhibit a cysteine protease", or a "cysteine protease inhibiting amount" of compound, thereby preventing or treating a parasitic infection, inflammation, or cancer invasion or growth in an individual.

The term "IC50" refers to the concentration of compound that results in half-maximal inhibition of enzyme.

By "parasitistatic" or "trypanostatic" or "*plasmodium*-static" or "*leishmania*-static" is intended that the intracellular cycle of the parasite is completed at a slower growth rate and the infected host cells survive longer.

The term "parasiticidal" or "trypanocidal" or "*plasmodium*-cidal" or "*leishmania*-cidal" means that the intracellular cycle of the parasite is not completed, therefore, leading to the death of the parasites.

For the thio semicarbazone compounds of the invention, the term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., C1-C10 means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —CH2CH2CH2CH2-, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O) 2-CH3, —CH═CH—O—CH3, —Si(CH3)3, —CH2-CH═N—OCH3, and —CH═CH—N(CH3)-CH3. Up to two heteroatoms may be consecutive, such as, for example, —CH2-NH—OCH3 and —CH2-O—Si(CH3)3. Similarly, the term "heteroalkylene" by itself or as part of another substituent means a divalent radical derived from heteroalkyl, as exemplified by —CH2-CH2-S—CH2CH2- and —CH2-S—CH2-CH2-NH—CH2-. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', ═O, ═NR', ═N—OR', —NR'R", —SR'], -halogen, —SiR'R"R'", —OC(O)R', —C(O)R', —CO2R', —CONR'R", —OC(O)NR'R", —NR"C(O)R', —NR'—C(O)NR"R'", —NR"C(O)2R', —NH—C(NH2)═NH, —NR'C(NH2)═NH, —NH—C(NH2)═NR', —S(O)R', —S(O)2R', —S(O)2NR'R", —CN and —NO2 in a number ranging from zero to (2m'+1), where m' is the total number of carbon atoms in such radical. R', R" and R'" each independently refer to hydrogen, unsubstituted (C1-C8)alkyl and heteroalkyl, unsubstituted aryl, aryl substituted with 1-3 halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF3 and —CH2CF3) and acyl (e.g., —C(O)CH3, —C(O)CF3, —C(O)CH2OCH3, and the like).

Similarly, substituents for the aryl and heteroaryl groups are varied and are selected from: -halogen, —OR', —OC(O) R', —NR'R", —SR', —R', —CN, —NO2, —CO2R', —CONR'R", —C(O)R', —OC(O)NR'R", —NR"C(O)R', —NR"C(O)2R', —NR'—C(O)NR"R'", —NH—C(NH2)=NH, —NR'C(NH2)=NH, —NH—C(NH2)=NR', —S(O)R', —S(O)2R', —S(O)2NR'R", —N3, —CH(Ph)2, perfluoro(C1-C4)alkoxy, and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl, and (unsubstituted aryl)oxy-(C1-C4)alkyl.

Two of the substituents on adjacent atoms of the aryl or heteroaryl ring may optionally be replaced with a substituent of the formula -T-C(O)—(CH2)q-U-, wherein T and U are independently —NH—, —O—, —CH2- or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH2-, —O—, —NH—, —S—, —S(O)—, —S(O)2-, —S(O)2NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH2)s-X—(CH2)t-, where s and t are independently integers of from 0 to 3, and X is —O—, —NR'—, —S—, —S(O)—, —S(O)2-, or —S(O)2NR'—. The substituent R' in —NR'— and —S(O)2NR'— is selected from hydrogen or unsubstituted (C1-C6)alkyl.

As used herein, the term "heteroatom" is meant to include oxygen (O), nitrogen (N), sulfur (S) and silicon (Si).

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Assays for Thio Semicarbazone and Semicarbazone Inhibitors of Cysteine Proteases The compounds of the invention are screened for effectiveness against cathepsin-L like cysteine proteases in vitro and for effectiveness in disrupting the infectious life cycle of a parasite or malignancy potential of a cancer cell in cell culture and in vivo disease model systems.

For in vitro cysteine protease inhibition determinations, a compound's effectiveness can be given by an IC50 value. In these assays, the enzyme to be inhibited (e.g., a cruzain or cruzipain, a rhodesain, a brucipain, a congopain, a falcipain, CPB2.8 Delta CTE, a cathepsin-L, cathepsin-B, a cathepsin-H, a cathepsin-K, a cathepsin-S) is first incubated with varying concentrations (about 20-50,000 nM) of a test compound. To this is added a short peptide substrate of the enzyme of 1 to 10 amino acids, usually a di- or tri-peptide substrate, which is labeled with either a fluorogenic or chromogenic moiety. An exemplary chromogenic moiety is p-nitro-anilide (pNA). Fluorogenic labels are generally comprised of a fluorescent donor, such as ortho-aminobenzoic acid (Abz) or benzyloxycarbonyl (Z), and a fluorescent quencher, such as 7-(4-methyl)-coumarylamide (AMC), methyl-7-aminocoumarin amide (MCA), 7-amino-4-trifluoromethylcoumarin (AFC) or N-(ethylenediamine)-2,4-dinitrophenyl amide (EDDnp), where the donor and quencher are on either terminus of the peptide substrate. Exemplary peptide substrates include Phe- Arg, Arg-Arg, Phe-Arg-X (X=Ala, Arg), and Phe-X-Ser-Arg-Gln (X=Arg, 4-aminomethyl-phenylalanine (Amf), 4-aminomethyl-N-isopropyl-phenylalanine (Iaf), 4-piperidinyl-alanine (Ppa) or 4-aminocyclohexyl-alanine (Aca)). Cleavage of the labeled substrate induces a chromogenic or fluorescent signal that is measured using spectrophotometer or a spectrofluorometer, respectively. Signals induced in the presence of varying concentrations of test compound are measured in comparison to a positive control of enzyme and substrate and a negative control of enzyme in diluent (e.g., DMSO). Spontaneous cleavage of substrate is measured in controls with substrate alone. IC50 values are determined graphically using compound inhibitor concentrations in the linear portion of a plot of inhibition versus log [I]. Inhibition of a target protease is achieved when the IC50 value is less than about 1000 nM, preferably less than about 500, 300 or 100 nM, more preferably less than about 90, 80, 70, 60, 50, 40, 30, 20 or 10 nM.

Anti-parasitic capacities of the compounds can be measured using cell culture assays. Cultured mammalian cells that are susceptible to infection by a target protozoan, such as for example, macrophages, erythrocytes, lymphocytes, fibroblasts or other cutaneous cells, hepatocytes, cardiocytes or myocytes are infected with infectious parasitic bodies, such as trypomastigotes to introduce trypanosome infection, merozoites to introduce *plasmodium* infection, or promastigotes to introduce *leishmania* infection. The culture medium is replaced to remove superfluous infectious parasitic bodies and to add test protease inhibitor compounds. Positive or treated control cultures are given a known parasitic inhibitor. For example, N-methyl piperazine-Phe-homoPhe-vinyl sulfone phenyl (N-Pip-F-hF-VSPh) is known to inhibit trypanosomes. Negative or untreated control cultures are given only diluent (e.g., DMSO) in medium. Cultures are maintained for a time period that encompasses several intracellular cycles of the target parasite in untreated controls, usually about 30 days, but as long as 35, 40, 45 or 50 days or longer, as necessary. Cells are monitored, usually daily but this can be more or less often, for the presence or absence of parasitic infection, usually by contrast phase microscopy. The comparative effectiveness of each test protease inhibitor compound is determined from plots of the duration of the intracellular cycle of the target parasite in treated versus untreated control cultures (generally measured in days).

The ability of compounds of the present invention to inhibit cell invasiveness and migration can also be tested using cellular motility and cellular invasion assays. These assays are particularly applicable to measuring the inhibition of migration of cancer and inflammatory cells whose migration requires, at least in part, the catalytic activity of at least one cysteine protease such as a cathepsin-L, a cathepsin-B, a cathepsin-H, a cathepsin-K or a cathepsin-S. In vitro cellular motility assays are generally carried out using transwell chambers (available from Corning-Costar), with upper and lower culture compartments separated by filters, for example, polycarbonate filters with 8 µm pore size. In vitro cellular invasion assays are conducted using matrigel precoated filters (for example, 100 µg/cm² matrigel on a filter with 8 µm pore size; available from Becton Dickinson). Prior to invasion assays, the matrigel matrix is reconstituted with serum-free cell culture medium. Excess media is removed from the filters and a chemoattractant is placed in the lower compartment of a transwell chamber, for example 5 µg/ml collagen I can be used for a tumor cell. A specified number of cells radiolabeled with ³H-thymidine are seeded onto the filter in motility assays or onto the reconstituted matrigel basement membrane for invasion assays. Cells passing through the filters and attaching to the lower sides of uncoated or matrigel-coated are harvested using trypsin/EDTA, and cell-bound radioactivity is measured in a liquid scintillation counter. The number of migrating cells is calculated by measuring the radioactivity of cells on the underside of a filter in comparison to the radioactivity of a parallel culture containing an identical number of cells to what was originally seeded on the top of the filter or matrigel coating.

The ability of the protease inhibitor compounds to prevent or treat parasitic infections or cancer cell or inflammatory cell invasion or migration in a host subject also can be tested using in vivo disease models. Experimental animal disease models for trypanosomiasis, *leishmania*, and malaria are known in the art. For example, murine models for trypanosomiasis are disclosed in Duthie and Kahn, *J Immunol* (2002) 168:5778, Mucci, et al, *Proc Natl Acad Sci* (2002) 99:3896, Zuniga, et al, *J Immunol* (2002) 168:3965 and in Guarner, et al (2001) *Am J Trop Med Hyg* 65:152. Murine models for *leishmania* are described in Rhee, et al, *J Exp Med* (2002) 195:1565, and in Hommel, et al, *Ann Trop Med Parasitol* (1995) 89 Supp 1:55. Murine models of malaria are published in Sanni, et al, *Methods Mol Med* (2002) 72:57, Renia, et al, *Methods Mol Med* (2002) 72:41, and Li, et al, *Med Microbiol Immunol* (2001) 189:115. In mouse parasitic disease models, for example, infected mice are administered a test compound of the present invention, and then monitered for amelioration or abatement of infection in comparison to infected, but untreated control mice. Alternatively, uninfected mice are treated with a test compound and then inoculated with a infectious parasitic body to determine the capacity of the compound to prevent parasitic infection. Disease models for cancer and inflammation are also well documented in the published literature. Murine disease models for human cancers require immunodeficient mice (reviewed in Bankert, et al, *Front Biosci* (2002) 7:c44 and in Hann and Balmain, *Curr Opin Cell Biol* (2001) 13:778). Additional animal cancer models are discussed in Bast, et al, *Cancer Medicine*, 5th Ed., B. C. Decker, Hamilton, Ontario, Canada).

Preparation of Thio Semicarbazone and Semicarbazone Inhibitors of Cysteine Proteases and Cyclized Pyrazoline Analogues Synthesis of Thio Semicarbazones and Semicarbazones. Thio Semicarbazones and Semicarbazones can be synthesized according to Scheme 1. Refluxing aldehyde or ketone with a thio semicarbazide generates thio semicarbazones. For aldehydes, the reaction is usually complete in less than 3 h and no acetic acid is required. For ketones, the reaction is usually run overnight with 1% acetic acid. Yields are generally greater than 90% except with a few specific ketones such as the 2-substituted aryl ketones. Synthesis of semicarbazones is done at room temperature. A sodium acetate solution of semicarbazide hydrochloride salt is added to the ethanol solution of aldehyde or ketone (Pandeya, S. N. et al., *Pharmacol Res.*, 37:17-22 (1998)). The product usually precipitates out with good yield.

SCHEME 1

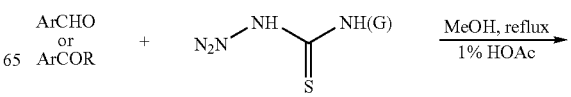

-continued

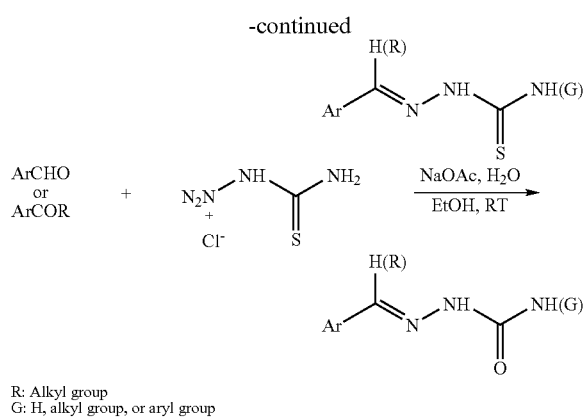

R: Alkyl group
G: H, alkyl group, or aryl group

Synthesis of the Cyclized Pyrazoline Analogues. Cyclized Pyrazoline analogues can be synthesized according to Scheme 2. The Mannich reaction of various ketones with formaldehyde and dimethylamine hydrochloride generates the Mannich base precursor (Wellinga, K. et al., *J. Agric. Food. Chem.*, 25:987-992 (1977)). The reaction is sensitive to both the amount of hydrochloric acid and the amount of solvent present. The reaction works best when a minimum amount of ethanol and 2 μL of acid/mmol ketone is applied. The methyl aryl ketones gave high yields above 80%, while the yields for other alkyl aryl ketones in the Mannich reaction were lower in the range of 30-60%. However, the product mixture contained only unreacted starting material and the Mannich product. The unreacted starting material was recovered for repetitive use. Condensation and cyclization of the precursor with the thio semicarbazide generates the cyclized pyrazoline analogues with yields between 20% and 50% without optimization. The cyclization also works in the substituted thio semicarbazide but with a lower yield.

Figure 13:
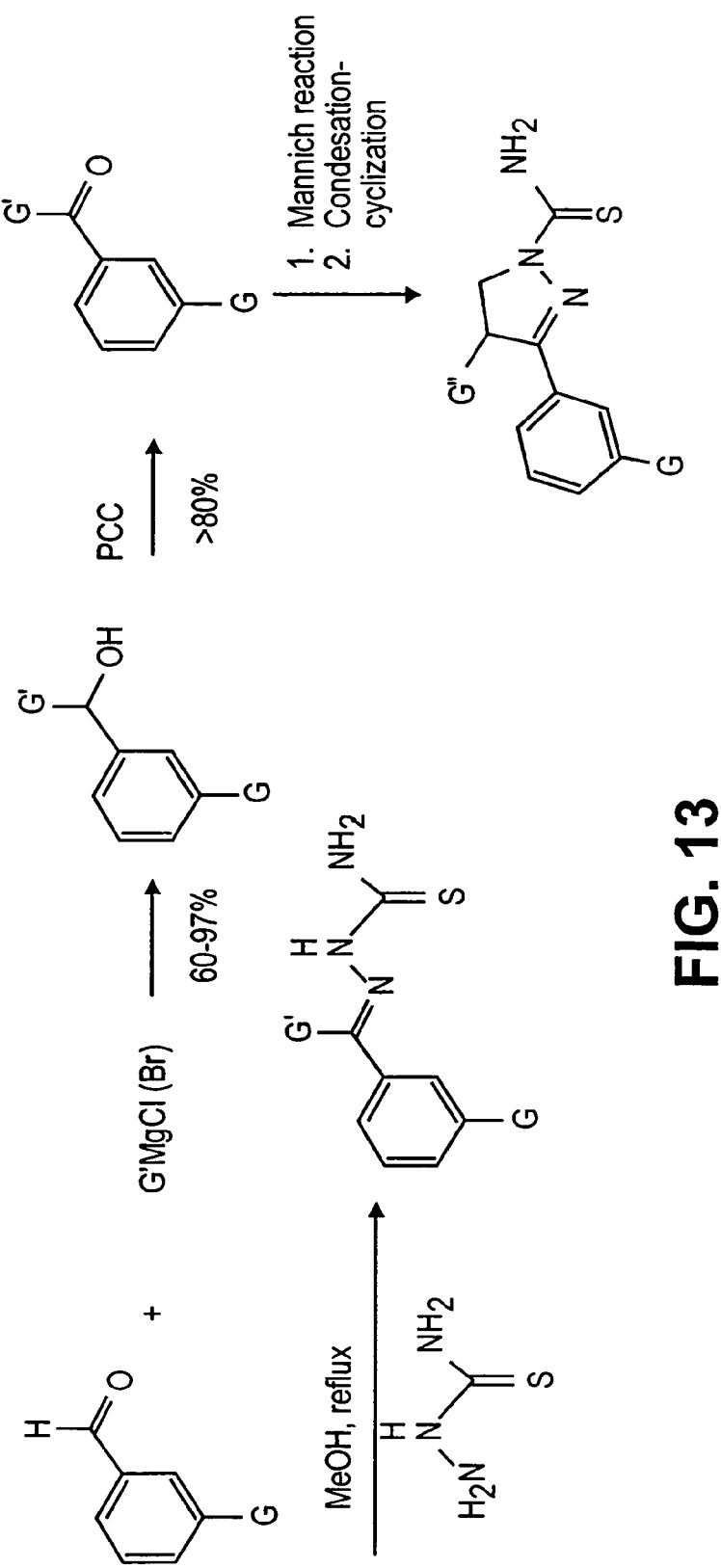
FIG. 13 shows the synthesis of compounds with additional C5-side chain variations.

Synthesis of the Various C5-Substituted Thio Semicarbazones and Pyrazolines. The C5-side chain is introduced through a Grignard reaction of the suitable aldehyde with the Grignard reagent containing the C5-side chain group in 60-97% yield. The resulting alcohol is oxidized with PCC in higher than 80% yield. Then thio semicarbazones and pyrazolines can be made through the previous routes. See synthesis schemes in FIG. 13.

SCHEME 2

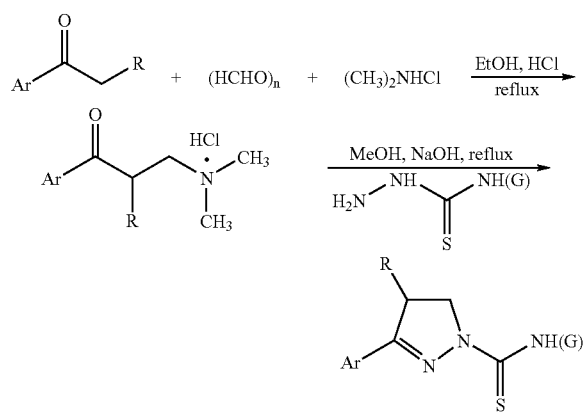

R: H, CH3
G: H, alkyl group, or aryl group

Administration and Pharmaceutical Compositions

Pharmaceutically and physiologically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17th ed., 1989). Suitable methods of administration include oral, nasal, rectal, and parenteral administration. Other delivery methods known to those of skill in the art can be used, e.g., liposomes, microspheres, and the like. The compounds of the invention can also be forumulated as prodrugs for ease of delivery.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of pain, the compounds utilized in the pharmaceutical method of the invention are administered at a therapeutically or prophylaticlaly effective dose, e.g., the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds of the invention can be administered in combination with other therapeutic compounds, either in the same pharmaceutical preparation, or in separate pharmaceutical preparations. The additional therapeutic or prophylactic compounds may be used to treat the same disease as the compound of the invention, e.g., a parasitic disease, a protozoan disease, or a cancer, or can be used to treat a second disease other than the disease treated by the compound of the invention. One or more compounds of the invention can be administered in the same pharmaceutical composition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Determination of the Characteristics of the Compounds

Melting points were determined in open capillaries with a Büchi melting point apparatus, B-540 (Switzerland). Infrared spectra were recorded in an Impact 400 spectrophotometer for a representative set of compounds. $^1$H NMR spectra were obtained with a Varian Inova-400 NMR spectrometer. Unless otherwise noted, all spectra were recorded with DMSO as solvent. Splitting patterns are designated as follows: s, singlet; br s, broad singlet; d, doublet; t, triplet; q, quartet; m, multiplet. Coupling constants (J) are given in hertz. Mass spectral analyses are performed at the Mass Spectrometry facility, University of California, San Francisco. Elemental analyses are carried out by Atlantic Microlab, Inc., Norcross, Ga. Unless otherwise stated, yields for the reactions are higher than 90%.

Example 2

General Procedure for the Preparation of Thio Semicarbazones

Aldehyde or ketone (0.5 mmol) and thio semi-carbazide (0.5 mmol) was added to a dry flask. The mixture was dissolved in 10 mL of anhydrous MeOH. For ketone, 1% acetic acid (0.1 mL) was also added to the reaction. The reaction was heated to reflux under nitrogen. Thin Layer Chromatography (TLC) was used to monitor whether the reaction was complete. The reaction time ranged from 3 h for aldehydes to overnight for ketones. The solvent was removed in vacuo, and the resulting solid was rinsed or recrystallized.

Example 3

Characteristics of the Thio Semicarbazone Compounds

Data for 4-(Phenylethynyl)thiophene-2-carboxyaldehyde Thio Semicarbazone (1a): mp 197.6-199.6° C.; $^1$H NMR δ 7.42 (m, 3H), 7.52 (m, 2H), 7.60 (s, 1H), 7.66 (br s, 1H), 7.95 (s, 1H), 8.19 (br s, 1H), 8.25 (s, 1H), 11.52 (s, 1H); HRMS (EI) m/z (M+) calcd for $C_{14}H_{11}N_3S_2$ 285.0394, found 285.0403.

Data for 5-(4-Chlorophenyl)-2-furancarboxaldehyde Thio Semicarbazone (1b): mp 199.2-200.8° C.; $^1$H NMR d 7.06 (d, 1H, J=3.2), 7.16 (d, 1H, J=3.6), 7.49 (d, 2H, J=8.4), 7.77 (br s, 1H), 7.85 (d, 2H, J=8.0), 7.96 (s, 1H), 8.28 (br s, 1H), 11.50 (s, 1H); HRMS (EI) m/z (M$^+$) calcd for $C_{12}H_{10}ClN_3OS$ 279.0233, found 279.0237.

Data for 5-(2-Methoxyphenyl)-2-furancarboxaldehyde Thio Semicarbazone (1c): mp 209.5-211.1° C.; IR (neat, cm$^{-1}$) 3389, 3234, 3138, 3051, 2983, 2930, 2839, 1603, 1545, 1487, 1343, 1299, 1241, 1101, 1019, 923, 845, 797, 759; $^1$H NMR δ 3.92 (s, 3H), 7.04 (m, 3H), 7.13(d, 1H, J=8.8), 7.33 (t, 1H, J=7.8), 7.76 (br s, 1H), 7.94 (d, 1H, J=7.6), 7.97 (s, 1H), 8.24 (br s, 1H), 11.46 (s, 1H); HRMS (EI) m/z (M$^+$) calcd for $C_{13}H_{13}N_3O_2S$ 275.0728, found 275.0720.

Data for 2-(1-Methyl-3-trifluoromethyl)pyrazol-5-yl)-thiophene-5-carboxaldehyde Thio Semicarbazone (1d): mp 222.4° C. dec; $^1$H NMR δ 4.05 (s, 3H), 7.06 (s, 1H), 7.52 (m, 2H), 7.62 (br s, 1H), 8.23 (s. 1H), 8.28 (br s, 1H), 11.57 (s, 1H); HRMS (EI) m/z (M$^+$) calcd for $C_{11}H_{10}F_3N_5S_2$ 333.0330, found 333.0337.

Data for 5-(3-Chlorophenyl)-2-furancarboxaldehyde Thio Semicarbazone (1e): mp 198.8-199.8° C.; $^1$H NMR δ 7.07 (d, 1H, J=3.6), 7.24 (d, 1H, J=3.6), 7.38 (d, 1H, J=8.0), 7.46 (m, 1H), 7.79 (d, 1H, J=8.0), 7.83 (br s, 1H), 7.89 (d, 1H, J=1.6), 7.96 (s, 1H), 8.28 (br s, 1H), 11.51 (s, 1H); HRMS (EI) m/z (M$^+$) calcd for $C_{12}H_{10}ClN_3OS$ 279.0233, found 279.0231.

Data for 5-(4-Bromophenyl)-2-furancarboxaldehyde Thio Semicarbazone (1f): $^1$H NMR (isomer ratio 3:1) (major isomer) δ 7.14 (dd, 1H, J=1,2, 3,6), 7.29 (d, 1H, J=1.2), 7.30 (s, 1H), 7.72 (m, 2H), 7.77 (m, 2H), 8.14 (br s, 1H), 8.61 (br s, 1H), 10.53 (s, 1H); (minor isomer) a 7.06 (d, 1H, J=2.4), 7.17 (m, 1H), 7.62 (d, 2H, J=7.6), 7.77 (m, 3H), 7.96 (s, 1H), 8.28 (br s, 1H), 11.50 (s, 1H); HRMS (EI) m/z (M$^+$) calcd for $C_{12}H_{10}BrN_3OS$ 322.9728, found 322.9723.

Data for 1-(Phenylsulfonyl)-2-pyrrolecarboxaldehyde Thio Semicarbazone (1 g): mp dec upon heating; $^1$H NMR δ 6.44 (t, 1H, J=3,4), 7.10 (d, 1H, J=2.0), 7.55 (s, 1H), 7.68 (t, 2H, J=7.8), 7.77 (t, 1H, J=7.4), 7.81 (br s, 1H), 7.96 (d, 2H, J=8.0), 8.17 (br s, 1H), 8.49 (s, 1H), 11.49 (s, 1H); HRMS (EI) m/z (M+) calcd for $C_{12}H_{12}N_4O_2S_2$ 308.0402, found 308.0407.

Data for 4'-Morpholinoacetophenone Thio Semicarbazone (1 h): mp 231.2-232.8° C.; $^1$H NMR δ 2.23 (s, 3H), 3.16 (t, 4H, J=4.8), 3.73 (t, 4H, J=4.8), 6.90 (d, 2H, J=8.8), 7.79 (d, 2H, J=8.8), 7.80 (s, 1H), 8.14 (br s, 1H), 10.04 (s, 1H); HRMS (EI) m/z (M$^+$) calcd for $C_{13}H_{18}N_4OS$ 278.1201, found 278.1210.

Data for 3'-Bromopropiophenone Thio Semicarbazone (1i): mp 144.3-144.1° C.; IR (neat, cm$^{-1}$) 3413, 3238, 3144, 3059, 2974, 2920, 1584, 1509, 1470, 1420, 1280, 1115, 1051, 857, 787; $^1$H NMR δ 0.99 (t, 3H, J=7.4), 2.85 (q, 2H, J=7.6), 7.33 (t, 1H, J=8.0), 7.55 (d, 1H, J=8.0), 7.85 (d, 1H, J=7.6), 8.04 (br s, 1H), 8.13 (s, 1H), 8.26 (br s, 1H), 10.30 (s, 1H); HRMS (EI) m/z (M$^+$) calcd for $C_{10}H_{12}BrN_3S$ 284.9935, found 284.9936. Anal. ($C_{10}H_{12}BrN_3S$)C, H, Br, N, S.

Data for 3-Hydroxy-4-methoxybenzaldehyde Thio Semicarbazone (1j): mp 175.3-177.5° C.; $^1$H NMR δ 3.79 (s, 3H), 6.92 (d, 1H, J=8.4), 7.10 (dd, 1H, J=1.6, 8.4), 7.24 (d, 1H, J=2.0), 7.78 (br s, 1H), 7.90 (s, 1H), 8.06 (br s, 1H), 9.03 (s, 1H), 11.24 (s, 1H); HRMS (EI) m/z (M$^+$) calcd for $C_9H_{11}N_3O_2S$ 225.0572, found 225.0566.

Data for 6'-Methoxy-2'-propiononaphthone Thio Semicarbazone (1k): mp 170.5-171.2° C.; $^1$H NMR δ 1.07 (t, 3H, J=7.4), 2.96 (q, 2H, J=7.4), 3,87 (s, 3H), 7.17 (dd, 1H, J=2.4, 8.8), 7.33 (d, 1H, J=2.4), 7.77 (d, 1H, J=8.8), 7.89 (d, 1H, J=8.8), 7.98 (br s, 1H), 8.19 (d, 1H, J=8.8), 8.26 (s, 1H), 8.30 (br s, 1H), 10.32 (s, 1H); HRMS (EI) m/z (M$^+$) calcd for $C_{15}H_{17}N_9OS$ 287.1092, found 287.1090.

Data for 4-Dimethylamino-1-naphthaldehyde Thio Semicarbazone (1l): mp 170.5-171.2° C.; $^1$H NMR δ 2.87 (s, 6H), 7.10 (d, 1H, J=8.0), 7.55 (m, 1H), 7.61 (m, 1H), 7.83 (br s, 1H), 8.03 (d, 1H, J=8.0), 8.18 (m, 2H), 8.42 (d, 1H, J=8.4), 8.78 (s, 1H), 11.32 (s, 1H); HRMS (EI) m/z (M$^+$) calcd for $C_{14}H_{16}N_4S$ 272.1096, found 272.1094.

Data for 1-Methylindole-3-carboxaldehyde Thio Semicarbazone (1m): mp 200.3-201.2° C.; $^1$H NMR δ 3.80 (s, 3H), 7.15 (t, 1H, J=7.4), 7.25 (t, 1H, J=7.6), 7.40 (br s, 1H), 7.47 (d, 1H, J=8.0), 7.79 (s, 1H), 8.00 (br s, 1H), 8.22 (d, 1H, J=7.6), 8.26 (s, 1H), 11.13 (s, 1H); HRMS (EI) m/z (M+) calcd for $C_{11}H_{12}N_4S$ 232.0783, found 232.0786.

Data for 2-Methoxy-1-naphthaldehyde Thio Semicarbazone (1n): mp 156.2-157.6° C.; $^1$H NMR δ 3.96 (s, 3H), 7.40 (t, 1H, J=7.4), 7.48 (d, 1H, J=9.2), 7.50 (br s, 1H), 7.56 (t, 1H, J=7.8), 7.88 (d, 1H, J=8.0), 8.02 (d, 1H, J=9.2), 8.20 (s, 1H), 8.80 (s, 1H), 8.92 (d, 1H, J=8.8), 11.48 (s, 1H); HRMS (EI) m/z (M$^+$) calcd for $C_{13}H_{13}N_3OS$ 259.0779, found 259.0772.

Data for 3'-Chloropropiophenone Thio Semicarbazone (2a): mp 136.6-138.3° C.; IR (neat, cm$^{-1}$)3408, 3203, 3155, 2970, 2941, 1598, 1511, 1472, 1418, 1301, 1233, 1112, 1053, 1004, 859, 791; $^1$H NMR δ 0.98 (t, 3H, J=7.4), 2.86 (q, 2H, J=7.6), 7.41 (m, 2H), 7.82 (m, 1H), 8.03 (s, 1H), 8.08 (br s, 1H), 8.31 (brs, 1H), 10.36 (s, 1H); HRMS (EI) m/z (M$^+$) calcd for $C_{10}H_{12}ClN_3S$ 241.0440, found 241.0449.

Data for 3'-Trifluoromethylpropiophenone Thio Semicarbazone (2b): mp 156.0-157.9° C.; IR (neat, cm$^{-1}$) 3427, 3272, 3155, 3053, 2975, 2941, 1618, 1525, 1481, 1345, 1306, 1189, 1146, 1078, 864, 810, 703; $^1$H NMR δ 1.00 (t, 3H, J=7.4), 2.92 (q, 2H, J=7.4), 7.61 (t, 1H, J=7.8), 7.72 (d, 1H, J=7.6), 8.11 (br s, 1H), 8.20 (s, 2H), 8.35 (br s, 1H), 10.42 (s, 1H); HRMS (EI) m/z (M$^+$) calcd for $C_{11}H_{12}F_3N_3S$ 275.0704, found 275.0709. Anal. ($C_{11}H_{12}F_3N_3S$)C, H, F, N, S.

Data for 3'-Fluoropropiophenone Thio Semicarbazone (2c): mp 138.8-139.5° C.; $^1$H NMR δ 0.99 (t, 3H, J=7.6), 2.86 (q, 2H, J=7.6), 7.20 (dt, 1H, J=2.4, 8.6), 7.43 (m, 1H), 7.69 (d, 1H, J=8.0), 7.87 (d, 1H, J=11.2), 8.07 (br s, 1H), 8.31 (br s, 1H), 10.36 (s, 1H); HRMS (EI) m/z (M$^+$) calcd for $C_{10}H_{12}FN_3S$ 225.0736, found 225.0738.

Data for Propiophenone Thio Semicarbazone (2d): mp 116.8-117.9; $^1$H NMR δ 1.01 (t, 3H,J=7.6), 2.86 (q, 2H,J=7.6), 7.38 (m, 3H), 7.89 (m, 3H), 8.22 (brs, 1H), 10.27 (s, 1H); HRMS (EI) m/z (M$^+$) calcd for $C_{10}H_{13}N_3S$ 207.0830, found 207.0826.

Data for 4'-Bromopropiophenone Thio Semicarbazone (2e): mp 171.3-173.0° C.; $^1$H NMR δ 0.98 (t, 3H, J=7.4), 2.84 (q, 2H, J=7.4), 7.55 (d, 2H, J=8.4), 7.88 (d, 2H, J=8.4), 7.97 (br s, 1H), 8.31 (br s, 1H), 10.38 (s, 1H); HRMS (EI) m/z (M$^+$) calcd for $C_{10}H_{12}BrN_3S$ 284.9935, found 284.9938.

Data for 4'-Chloropropiophenone Thio Semicarbazone (2f): yield 60%; mp 175.1-176.8° C.; $^1$H NMR δ 0.99 (t, 3H, J=7.6), 2.84 (q, 2H, J=7.6), 7.41 (d, 2H, J=8.8), 7.95 (d, 2H, J=8.4), 7.96 (br s, 1H), 8.30 (br s, 1H), 10.37 (s, 1H); HRMS (EI) m/z (M$^+$) calcd for $C_{10}H_{12}ClN_3S$ 241.0440, found 241.0447.

Data for 4'-Methoxypropiophenone Thio Semicarbazone (2g): mp 117.8-119.8° C.; $^1$H NMR δ 0.99 (t, 3H, J=7.6), 2.83 (q, 2H, J=7.6), 3.78 (s, 3H), 6.92 (d, 2H, J=9.2), 7.85 (br s, 1H), 7.86 (d, 2H, J=8.8), 8.19 (brs, 1H), 10.21 (s, 1H); HRMS (EI) m/z (M$^+$) calcd for $C_{10}H_{15}N_3OS$ 237.0936, found 237.0933.

Data for 3',5'-bis(trifluoromethyl)propiophenone Thio Semicarbazone (2h): mp 188.0-190.2° C.; IR (neat, cm$^{-1}$) 3245, 3153, 2982, 2936, 1596, 1508, 1466, 1392, 1281, 1171, 1126, 893, 866; $^1$H NMR δ 0.99 (t, 3H, J=7.6), 2.98 (q, 2H, t, 3H, J=7.6), 8.07 (s, 1H), 8.33 (br s, 1H), 8.43 (br s, 1H), 8.49 (s, 2H), 10.51 (s, 1H); HRMS (EI) m/z (M+H$^+$) calcd for $C_{12}H_{12}F_6N_3S$ 344.0656, found 344.0671.

Data for 3',4'-Dichloropropiophenone Thio Semicarbazone (2i): mp 185.6-186.4° C.; IR (neat, cm$^{-1}$) 3420, 3249, 3150, 3041, 2980, 2942, 1603, 1513, 1475, 1390, 1300, 1101, 1063, 888, 860, 793; $^1$H NMR δ 0.98 (t, 3H, J=7.6), 2.86 (q, 2H. J=7.6), 7.61 (d, 1H, J=8.8), 7.85 (dd, 1H, J=2.0, 8.6), 8.12 (br s, 1H), 8.22 (d, 1H, J=2.0) 8.30 (br s, 1H), 10.35 (s, 1H); FIRMS (EI) m/z (M$^+$) calcd for $C_{10}H_{11}Cl_2N_3S$ 275.0051, found 275.0053.

Data for 2',4'-Dichloropropiophenone Thio Semicarbazone (2j): mp 171.8-173.0° C.; $^1$H NMR δ 1.04 (t, 3H, J=7.6), 2.49 (q, 2H, J=7.6), 7.33 (d, 1H, J=8.4), 7.53 (dd, 1H, J=2.0, 8.4), 7.75 (d, 1H, J=2.0), 7.77 (br s, 1H), 8.26 (br s, 1H), 9.42 (s, 1H); HRMS (EI) m/z (M$^+$) calcd for $C_{10}H_{11}Cl_2N_3S$ 275.0051, found 275.0049.

Data for 3'-Methoxyacetophenone Thio Semicarbazone (2k): mp 195.1-196.7° C.; $^1$H NMR δ 2.28 (d, 3H, J=3.2), 3.79 (d, 3H, J=2.8), 6.95 (d, 1H, J=8.0), 7.29 (dt, 1H, J=2.8, 8.0), 7.44 (m, 2H), 7.88 (br s, 1H), 8.21 (br s, 1H), 10.12 (s, 1H); HRMS (EI) m/z (M$^+$) calcd for $C_{10}H_{13}N_3OS$ 223.0779, found 223.0777.

Data for 2'-Bromoacetophenone Thio Semicarbazone (2l): yield 40%; mp 144.5-146.2° C.; $^1$H NMR δ 2.27 (s, 3H), 7.31 (m, 1H), 7.42 (m, 2H), 7.60 (br s, 1H), 7.65 (d, 1H, J=8.0), 8.24 (br s, 1H), 10.34 (s, 1H); HRMS (EI) m/z (M$^+$) calcd for $C_9H_{10}BrN_3S$ 270.9779, found 270.9775.

Data for 2'-Chloroacetophenone Thio Semicarbazone (2m): yield 45%; mp 155.8-156.7° C.; $^1$H NMR δ 2.28 (s, 3H), 7.38 (m, 2H), 7.49 (m, 2H), 7.62 (br s, 1H), 8.24 (br s, 1H), 10.34 (s, 1H); HRMS (EI) m/z (M$^+$) calcd for $C_9H_{10}ClN_3S$ 227.0284, found 227.0289.

Data for 2,3-Dichlorobenzaldehyde Thio Semicarbazone (2n): mp 232.3-233.6° C.; $^1$H NMR δ 7.37 (t, 1H, J=8.0), 7.65 (m, 1H), 8.17 (br s, 1H), 8.29 (d, 1H, J=8.0), 8.35 (br s, 1H), 8.48 (s, 1H), 11.67 (s, 1H); HRMS (EI) m/z (M$^+$) calcd for $C_8H_7Cl_2N_3S$ 246.9738, found 246.9730.

Data for 3,5-Dichlorobenzaldehyde Thio Semicarbazone (2o): mp 234.1-235.5° C.; $^1$H NMR δ 7.57 (t, 1H, J=1.6), 7.93 (d, 2H, J=1.6), 7.96 (s, 1H), 8.31 (br s, 1H), 11.59 (s, 1H); HRMS (EI) m/z (M$^+$) calcd for $C_8H_7Cl_2N_3S$ 246.9738, found 246.9737.

Data for 2-Trifluoromethylbenzaldehyde Thio Semicarbazone (2p): mp 248.3-249.4° C.; $^1$H NMR δ 7.58 (t, 1H, J=7.6), 7.68 (t, 1H, J=7.6), 7.75 (d, 1H, J=8.0), 8.15 (br s, 1H), 8.35 (br s, 1H), 8.43 (s, 1H), 8.50 (d, 1H, J=8.0), 11.67 (s, 1H); HRMS (EI) m/z (M$^+$) calcd for $C_9H_8F_3N_3S$ 247.0391, found 247.0391.

Data for 3-Bromobenzaldehyde Thio Semicarbazone (3a): mp 200.6-210.9° C.; IR (neat, cm$^{-1}$) 3388, 3233, 3149, 3024, 2984, 2805, 1604, 1534, 1467, 1355, 1310, 1220, 1101, 941, 897, 832, 792; $^1$H NMR δ 7.34 (t, 1H, J=7.6), 7.55 (d, 1H, J=7.2), 7.68 (d, 1H, J=7.6), 7.99 (s, 1H), 8.18 (s, 2H), 8.24 (br s, 1H), 11.49 (s, 1H); HRMS (EI) m/z (M$^+$) calcd for $C_8H_8BrN_3S$ 256.9622, found 256.9618.

Data for 3'-Bromoacetophenone Thio Semicarbazone (3b): mp 174.2-174.9° C.; IR (neat, cm$^{-1}$) 3428, 3263, 3144, 3059, 1604, 1524, 1310, 1116, 871, 802, 732; $^1$H NMR δ 2.27 (s, 3H), 7.33 (t, 1H, J=8.0), 7.55 (dd, 1H, J=1.0, 8.0), 7.88 (d, 1H, J=8.0), 8.10 (br s, 1H), 8.18 (s, 1H), 8.31 (br s, 1H), 10.22 (s, 1H); HRMS (EI) m/z (M$^+$) calcd for $C_9H_{10}BrN_3S$ 270.9779, found 270.9778.

Data for 3-Trifluoromethylbenzaldehyde Thio Semicarbazone (3c): mp 220.7-221.7° C.; $^1$H NMR δ 7.62 (t, 1H, J=7.6), 7.71 (d, 1H, J=8.0), 8.02 (d, 1H, J=7.6), 8.10 (s, 1H), 8.25 (br s, 1H), 8.26 (s, 1H), 8.28 (br s, 1H), 11.55 (s, 1H); HRMS (EI) m/z (M$^+$) calcd for $C_9H_8F_3N_3S$ 247.0391, found 247.0395.

Data for 3-Trifluoromethylacetophenone Thio Semicarbazone (3d): mp 197.9-201.2° C.; $^1$H NMR δ 2.33 (s, 3H), 7.60 (t, 1H, J=7.6), 7.72 (d, 1H, J=7.6), 8.13 (br s, 1H), 8.22 (m, 2H), 8.34 (br s, 1H), 10.29 (s, 1H); HRMS (EI) m/z (M$^+$) calcd for $C_{10}H_{10}F_3N_3S$ 261.0548, found 261.0545.

Data for 3,5-Bis(trifluoromethyl)benzaldehyde Thio Semicarbazone (3e): mp 229.8-230.3° C.; $^1$H NMR δ 8.04 (s, 1H), 8.16 (s, 1H), 8.38 (br s, 1H 8.46 (br s, 1H 8.54 (s, 2H), 11.71 (s, 1H); HRMS (EI) m/z (M$^+$) calcd for $C_{10}H_7F_6N_3S$ 315.0265, found 315.0269.

Data for 3',5'-Bis(trifluoromethyl)acetophenone Thio Semicarbazone (3f): mp 238° C. dec; $^1$H NMR δ 2.38 (s, 3H), 8.06 (s, 1H), 8.36 (br s, 1H), 8.42 (br s, 1H), 8.53 (s, 2H), 10.37 (s, 1H); HRMS (EI) m/z (M$^+$) calcd for $C_{11}H_9F_6N_3S$ 329.0421, found 321.0429.

Data for 3,4-Dichlorobenzaldehyde Thio Semicarbazone (3g): $^1$H NMR δ 7.64 (d, 1H, J=8.4), 7.71 (dd, 1H, J=1.8, 8.4), 7.98 (s, 1H), 8.24 (s, 1H), 8.27 (br s, 1H), 11.55 (s, 1H); HRMS (EI) m/z (M$^+$) calcd for $C_8H_7C_{12}N_3S$ 246.9738, found 246.9732.

Data for 3',4'-Dichloroacetophenone Thio Semicarbazone (3h): mp 196.0-197.9° C.; $^1$H NMR δ 2.27 (s, 3H), 7.61 (d, 1H, J=8.8), 7.88 (dd, 1H, J=0.8, 8.4), 8.17 (br s, 1H), 8.27 (s, 1H), 8.34 (br s, 1H), 10.27 (s, 1H); HRMS (EI) m/z (M$^+$) calcd for $C_9H_9Cl_2N_3S$ 260.9894, found 260.9891. Anal. ($C_9H_9$—$Cl_2N_3S$)C, H, Cl, N, S.

Data for 2-Acetyl-5-bromothiophene Thio Semicarbazone (3i): mp 205.1-207.3° C.; $^1$H NMR δ 2.27 (s, 3H), 7.19 (m, 1H), 7.32 (d, 1H, J=3.6), 7.49 (br s, 1H), 8.31 (br s, 1H), 10.37 (s, 1H); HRMS (EI) m/z (M$^+$) calcd for $C_7H_8BrN_3S_2$ 276.9343, found 276.9349.

Data for 2-Acetyl-5-chlorothiophene Thio Semicarbazone (3j): mp 237.1-238.2° C.; $^1$H NMR δ 2.27 (s, 3H), 7.09 (d, 1H, J=4.0), 7.36 (d, 1H, J=4.0), 7.48 (br s, 1H), 8.31 (br s, 1H), 10.38 (s, 1H); HRMS (EI) m/z (M$^+$) calcd for $C_7H_8ClN_3S_2$ 232.9848, found 232.9845.

Example 4

General Procedure for Synthesizing Cyclized Pyrazoline Analogues of Thio Semicarbazones Mannich Reaction. A 20 μL portion of concentrated hydrochloric acid was added to a mixture of ketone (10 mmol), paraformaldehyde (13 mmol, 390 mg), and dimethylamine hydrochloride (13 mmol, 1.059 g) in 5 mL of ethanol. The reaction was refluxed overnight under nitrogen. In some cases, precipitates formed and the product was obtained by filtration in ethanol. If no precipitate was formed, the solvent was removed. A few drops of HCl is added, and the mixture is worked up with dichloromethane and water. The dichloromethane layer was discarded. The aqueous layer was adjusted to basic and extracted with dichloromethane (3×). The dichloromethane layer was combined and dried. The product was obtained by removal of dichloromethane.

Cyclization. Thio semicarbazide or substituted thio semicarbazide (0.5 mmol) was dissolved in MeOH (5 mL) upon refluxing under nitrogen. Sodium hydroxide (50%) (0.18 mL) was added to the reaction. A warm methanol (5 mL) solution of the previous Mannich reaction product (0.5 mmol) was then added dropwise to the reaction mixture. After the reaction was refluxed for 1 h, methanol was removed at reduced pressure. The residue was dissolved in dichloromethane and washed with water. Evaporation of the solvent and purification through chromatography gave the cyclized analogues.

Example 5

Characteristics of the Cyclized Pyrazoline Analogues

Data for 3-(3-Bromophenyl)-2-pyrazoline-1-thiocarboxamide (4a): Mannich yield 84%, cyclization yield 24%; mp 172.9-174.5° C., $^1$H NMR δ 3.28 (t, 2H, J=10.0), 4.14 (t, 2H, J=10.0), 7.41 (t, 1H, J=8.0), 7.64 (d, 1H, J=8.4), 7.75 (d, 1H, J=8.0), 7.89 (br s, 1H), 8.00 (br s, 1H), 8.13 (s, 1H); HRMS (EI) m/z (M$^+$) calcd for $C_{10}H_{10}BrN_3S$ 282.9779, found 282.9780.

Data for 3-(3-Bromophenyl)-4-methyl-2-pyrazoline-1-thiocarboxamide (4b): Mannich yield 81%, cyclization yield 62%; mp 107.4-109.9° C.; IR (neat, cm$^{-1}$) 3430, 3240, 3139, 3064, 2954, 2924, 2859, 1589, 1497, 1466, 1366, 1086, 1006, 901, 790; $^1$H NMR δ 1.17 (d, 3H, J=7.2), 3.80 (m, 1H), 3.92 (dd, 1H, J=4.2, 11.6), 4.19 (t, 1H, J=11.6), 7.41 (t, 1H, J=8.0), 7.63 (m, 1H), 7.78 (d, 1H, 8.0), 7.94 (br s, 1H), 8.07 (br s, 1H), 8.16 (m, 1H); HRMS (EI) m/z (M+) calcd for $C_{11}H_{12}BrN_3S$ 296.9935, found 296.9926.

Data for 3-(3-Chlorophenyl)-2-pyrazoline-1-thiocarboxamide (4c): Mannich yield 87%, cyclization yield 25%; mp 154.3-157.0° C.; $^1H$ NMR δ 3.28 (t, 2H, J=9.2), 4.14 (t, 2H, J=10.0), 7.49 (m, 2H), 7.72 (d, 1H, J=7.2), 7.89 (br s, 1H), 7.99 (s, 2H); HRMS (EI) m/z (M+) calcd for $C_{10}H_{10}ClN_3S$ 239.0284, found 239.0284.

Data for 3-(3-Chlorophenyl)-4-methyl-2-pyrazoline-1-thiocarboxamide (4d): Mannich yield 44%, cyclization yield 47%; mp 131.3° C. dec; IR (neat, cm$^{-1}$) 3432, 3267, 3147, 3062, 2967, 2927, 2881, 1584, 1499, 1464, 1364, 1118, 1008, 908, 803, 743; $^1H$ NMR δ 1.17 (d, 3H, J=7.2), 3.80 (m, 1H), 3.94 (dd, 1H, J=4.4, 11.6), 4.19 (t, 1H, J=11.2), 7.50 (m, 2H), 7.75 (d, 1H, J=6.8), 7.93 (br s, 1H), 8.03 (s, 1H), 8.07 (br s, 1H); HRMS (EI) m/z (M+) calcd for $C_{11}H_{12}ClN_3S$ 253.0440, found 253.0447.

Data for 3-(3,4-Dichlorophenyl)-2-pyrazoline-1-thiocarboxamide (4e): Mannich yield 50%, cyclization yield 20%; mp 199.3-201.4° C.; IR (neat, cm$^{-1}$) 3427, 3233, 3140, 2921, 2843, 1598, 1501, 1467, 1379, 1102, 888, 815; $^1H$ NMR δ 3.28 (t, 3H, J=10.0), 4.15 (t, 2H, J=10.0), 7.74 (m, 2H), 7.94 (br s, 1H), 8.04 (br s, 1H), 8.16 (s, 1H); HRMS (EI) m/z (M+) calcd for $C_{10}H_9Cl_2N_3S$ 272.9894, found 272.9896.

Data for 3-(3,4-Dichlorophenyl)-4-methyl-2-pyrazoline-1-thiocarboxamide (4f): Mannich yield 28%, cyclization yield 52%; mp 171.2-172.7° C.; IR (neat, cm$^{-1}$) 3434, 3264, 3145, 3051, 2961, 2927, 2868, 1581, 1457, 1368, 1129, 1027, 907, 809; $^1H$ NMR δ 1.17 (d, 3H, J=7.2), 3.80 (m, 1H), 3.95 (dd, 1H, J=4.0, 11.6), 4.19 (t, 1H, J=11.6), 7.72 (d, 1H, J=8.0), 7.79 (d, 1H, J=8.4), 7.99 (br s, 1H), 8.10 (br s, 1H), 8.21 (s, 1H); HRMS (EI) m/z (M+) calcd for $C_{11}H_{11}C_{12}N_3S$ 287.0051, found 287.0052.

Data for 3-(3-Trifluoromethylphenyl)-2-pyrazoline-1-thiocarboxamide (4g): Mannich yield 61%, cyclization yield 30%; mp 159.2-161.1° C.; $^1H$ NMR δ 3.34 (t, 2H, J=10.4), 4.17 (t, 2H, J=10.0), 7.70 (t, 1H, J=7.6), 7.81 (d, 1H, J=8.0), 8.03 (m, 3H), 8.26 (s, 1H); HRMS (EI) m/z (M+) calcd for $C_{11}H_{10}F_3N_3S$ 273.0548, found 273.0542.

Data for 3-(3-Trifluoromethylphenyl)-4-methyl-2-pyrazoline-1-thiocarboxamide (4h): Mannich yield 40%, cyclization yield 35%; mp 120.8-121.9° C.; IR (neat, cm$^{-1}$) 3443, 3264, 3145, 3068, 2966, 2932, 2872, 1589, 1487, 1351, 1129, 907, 805; $^1H$ NMR δ 1.19 (d, 3H, J=6.8), 3.88 (m, 1H), 3.97 (dd, 1H, J=4.4, 11.2), 4.22 (t, 1H, J=11.2), 7.69 (t, 1H, J=7.6), 7.80 (d, 1H, J=7.6), 8.02 (br s, 1H), 8.08 (d, 1H, J=8.4), 8.11 (br s, 1H), 8.30 (s, 1H); HRMS (EI) m/z (M+) calcd for $C_{12}H_{12}F_3N_3S$ 287.0704, found 287.0701. Anal. ($C_{12}H_{12}F_3N_3S$)C, H, F, N, S.

For N1-amino-substituted compounds, only the data of the representative compounds are given.

Data for 3'-Bromopropiophenone N-Methyl Thio Semicarbazone (5a): yield 61%, with no acetic acid added during reaction; mp 156.6-158.0° C.; IR (neat, cm$^{-1}$) 3367, 3297, 3197, 3057, 2967, 2932, 1544, 1494, 1469, 1234, 1118, 1048, 793; $^1H$ NMR δ 0.98 (t, 3H, J=7.6); 2.87 (q, 2H, J=7.2), 3.03 (s, 3H), 7.36 (t, 1H, J=8.0), 7.57 (d, 1H, J=8.0), 7.87 (d, 1H, J=7.6), 8.11 (s, 1H), 8.53 (br s, 1H), 10.39 (s, 1H); HRMS (EI) m/z (M+) calcd for $C_{11}H_{14}BrN_3S$ 299.0092, found 299.0091.

Data for 3-(3-Bromophenyl)-2-pyrazoline-1-(N-methyl)thiocarboxamide (5b): cyclization yield 10%; $^1H$ NMR δ 2.98 (d, 3H, J=4.4), 3.26 (t, 2H, J=9.6), 4.15 (t, 2H, J=10.0), 7.43 (t, 1H, J=8.0), 7.64 (d, 1H, J=8.4), 7.74 (d, 1H, J=7.6), 8.13 (s, 1H), 8.48 (d, 1H, J=4.4); HRMS (EI) rdz (M+) calcd for $C_{11}H_{12}BrN_3S$ 296.9935, found 296.9939.

Data for 3'-Bromopropiophenone N-(4-Trifluoromethylphenyl) Thio Semicarbazone (5c): mp 153.7-155.7° C.; IR (neat, cm$^{-1}$) 3302, 3210, 2975, 2935, 1592, 1536, 1463, 1325, 1281, 1115, 840; $^1H$ NMR δ 1.04 (t, 3H, J=7.2), 2.95 (q, 2H, J=7.2), 7.38 (t, 1H, J=8.0), 7.61 (d, 1H, J=8.0), 7.72 (d, 2H, J=8.8), 7.86 (m, 2H), 7.94 (d, 1H, J=8.0), 8.17 (s, 1H), 10.30 (s, 1H), 10.98 (s, 1H); HRMS (EI) m/z (M–H) calcd for $C_{17}H_{15}Br^{81}F_3N_3S$ 430.0023, found 430.0009.

Data for 3-(3-Bromophenyl)-2-pyrazoline-1-(IL3-chlorophenyl)thiocarboxamide (5d): yield 35%; mp 197.5-198.8° C.; IR (neat, cm$^{-1}$) 3337, 3081, 2970, 1606, 1559, 1491, 1444, 1363, 1133, 878; $^1H$ NMR δ 3.36 (t, 2H, J=10.0), 4.25 (t, 2H, J=10.0), 7.19 (dd, 1H, J=1.2, 8.0), 7.38 (t, 1H, J=8.0), 7.45 (t, 1H, J=8.0), 7.58 (d, 1H, 8.0), 7.68 (dd, 1H, J=1.2, 8.0), 7.73 (t, 1H, J=1.6), 7.86 (d, 1H, J=8.0), 8.26 (t, 1H, J=1.6), 10.19 (s, 1H); HRMS (EI) m/z (M+) calcd for $C_{16}H_{13}Br^{81}ClN_3S$ 394.9682, found 394.9694.

Data for 3-(3-Chlorophenyl)-2-pyrazoline-1-(N-3-trifluoromethylphenyl)thiocarboxamide (5e): cyclization yield 6%; mp 151.8-152.9° C.; $^1H$ NMR δ 3.38 (t, 2H, J=9.6), 4.27 (t, 2H, 9.6), 7.56 (m, 4H), 7.83 (d, 1H, J=7.2), 7.95 (t, 1H, J=7.2), 8.00 (d, 1H, J=7.6), 8.14 (s, 1H), 10.31 (s, 1H); HRMS (EI) m/z (M+) calcd for $C_{17}H_{13}ClF_3N_3S$ 383.0471, found 383.0474.

Data for 3-(3-Bromophenyl)-2-pyrazoline-1-(N-hexyl)thiocarboxamide (5f): cyclization yield 18%; mp 117.0-118.2° C.; $^1H$ NMR δ 0.86 (m, 3H), 1.27 (m, 6H), 1.56 (m, 2H), 3.25 (t, 2H, J=10.4), 3.51 (q, 2H, J=6.8), 4.15 (t, 2H, J=10.4), 7.42 (t, 1H, J=7.6), 7.64 (d, 1H, J=7.6), 7.75 (d, 1H, J=7.6), 8.12 (d, 1H, J=1.2), 8.49 (t, 1H, J=5.6); HRMS (EI) m/z (M+) calcd for $C_{16}H_{22}BrN_3S$ 367.0718, found 367.0724.

Example 6

General Procedure for the Preparation of Semicarbazones

Semicarbazide hydrochloride (1 mmol) and sodium acetate (1 mmol) were dissolved in 1 mL of distilled water. The solution was slowly added to an ethanol (5 mL) solution of aldehyde or ketone (1 mmol) and the mixture stirred for 2 h. The resulting precipitate was filtered, washed with water and methanol, and dried. Only the data of the representative compounds are given.

Example 7

Characteristics of the Semicarbazones

Data for 3'-Bromopropiophenone Semicarbazone (6a): mp 182.4-184.2° C.; IR (neat, cm$^{-1}$) 3473, 3302, 3209, 3068, 2974, 1713, 1593, 1491, 1419, 1142, 1065, 831, 801; $^1H$ NMR δ 0.97 (t, 3H, J=7.6), 2.71 (q, 2H, J=7.6), 6.54 (br s, 2H), 7.31 (t, 1H, J=8.0), 7.51 (m, 1H), 7.79 (d, 1H, J=8.0), 8.03 (s, 1H), 9.53 (s, 1H); HRMS (EI) m/z (M+) calcd for $C_{10}H_{12}$—$BrN_3O$ 269.0164, found 269.0158.

Data for 3'-Bromoacetophenone Semicarbazone (6b): mp 229.3-231.3° C.; $^1H$ NMR δ 2.15 (s, 3H), 6.55 (br s, 2H), 7.31 (t, 1H, J=7.6), 7.51 (d, 1H, J=7.6), 7.80 (d, 1H, J=8.4), 8.04 (s, 1H), 9.37 (s, 1H); HRMS (EI) m/z (M+) calcd for $C_9H_{10}BrN_3O$ 255.0007, found 255.0000.

Data for 5-(3-Chlorophenyl)-2-furancarboxaldehyde Semicarbazone (6c): mp 192.1-194.8° C.; $^1H$ NMR δ 6.44 (s, 2H), 6.92 (d, 1H, J=3.6), 7.20 (d, 1H, J=3.6), 7.36 (dd, 1H, J=1.2, 8.0), 7.45 (t, 1H, J=8.0), 7.75 (d, 1H, J=6.8), 7.85 (s, 1H), 10.33 (s, 1H); HRMS (EI) m/z (M+) calcd for $C_{12}H_{10}$—$ClN_3O_2$ 263.0462, found 263.0467.

Example 8

Reduction of Thio Semicarbazone 1i to 1-(3'-bromophenyl)propylaminothiourea (Synthesis of 7a according to scheme 3)

Thio semicarbazone (100 mg) was dissolved in anhydrous methanol. Sodium borohydride (excess) was added in small portions every 30 min. The reaction was heated to reflux under nitrogen. The reaction was stopped when most of the starting material was reacted according to TLC. Then the reaction was worked up with saturated ammonium chloride solution and ethyl acetate. After concentration, chromatography gave pure 7a in 70% yield: mp 110.4-112.4° C.; IR (neat, cm$^{-1}$) 3403, 3224, 3144, 3064, 2965, 2930, 2870, 1589, 1470, 1270, 1066, 872, 787; $^1$H NMR δ 0.64 (t, 3H, J=7.2), 1.43 (m, 1H), 1.68 (m, 1H), 3.74 (m, 1H), 7.25 (t. 1H, J=7.6), 7.34 (d, 1H, J=7.6), 7.38 (br s, 1H), 7.43 (d, 1H, J=8.0), 7.57 (br s, 1H), 7.61 (s, 1H), 8.51 (s, 1H); HRMS (EI) m/z (M+H+) calcd for $C_{10}H_{14}BrN_3S$ 288.0170, found 288.0159.

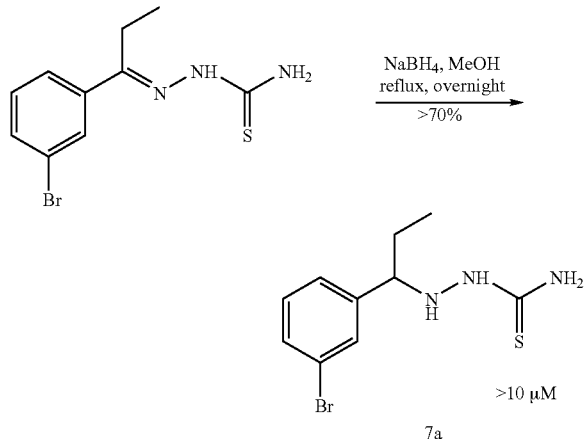

SCHEME 3

Example 9

Protease Inhibition Assay

Methods

IC$_{50}$ Determinations. Inhibitors were screened for effectiveness against the *T. cruzi* cathepsin L-like protease (cruzain) using purified recombinant protein. Cruzain (1 nM) was incubated with 20-50000 nM inhibitor in 100 mM sodium acetate-5 mM DTT buffer (pH 5.50, buffer A) for 5 min at room temperature. A 200 µL portion of Z-Phe-Arg-AMC (Bachem, K$_m$=1 µM) was added to the enzyme-inhibitor reaction to give a 20 µM substrate concentration. The increase in fluorescence (excitation at 355 nM and emission at 460 nM) was followed with an automated microtiter plate spectrofluorimeter (Molecular Devices, spectraMAX Gemini). Inhibitor stock solutions were prepared at 20 mM in DMSO, and serial dilutions were made in DMSO (0.7% DMSO in assay). Controls were performed using enzyme alone and enzyme with DMSO. IC$_{50}$ values were determined graphically using inhibitor concentrations in the linear portion of a plot of inhibition versus log [I] (seven concentrations were tested, and at least two were in the linear range).

The time dependence of inhibition was determined by incubating cruzain with inhibitors, DMSO, or enzyme alone at room temperature for time points between 90 s and 24 h. The enzymatic activity was determined as above.

Results

Thio Semicarbazones inhibit cruzain cysteine protease activity.

Figure 2:
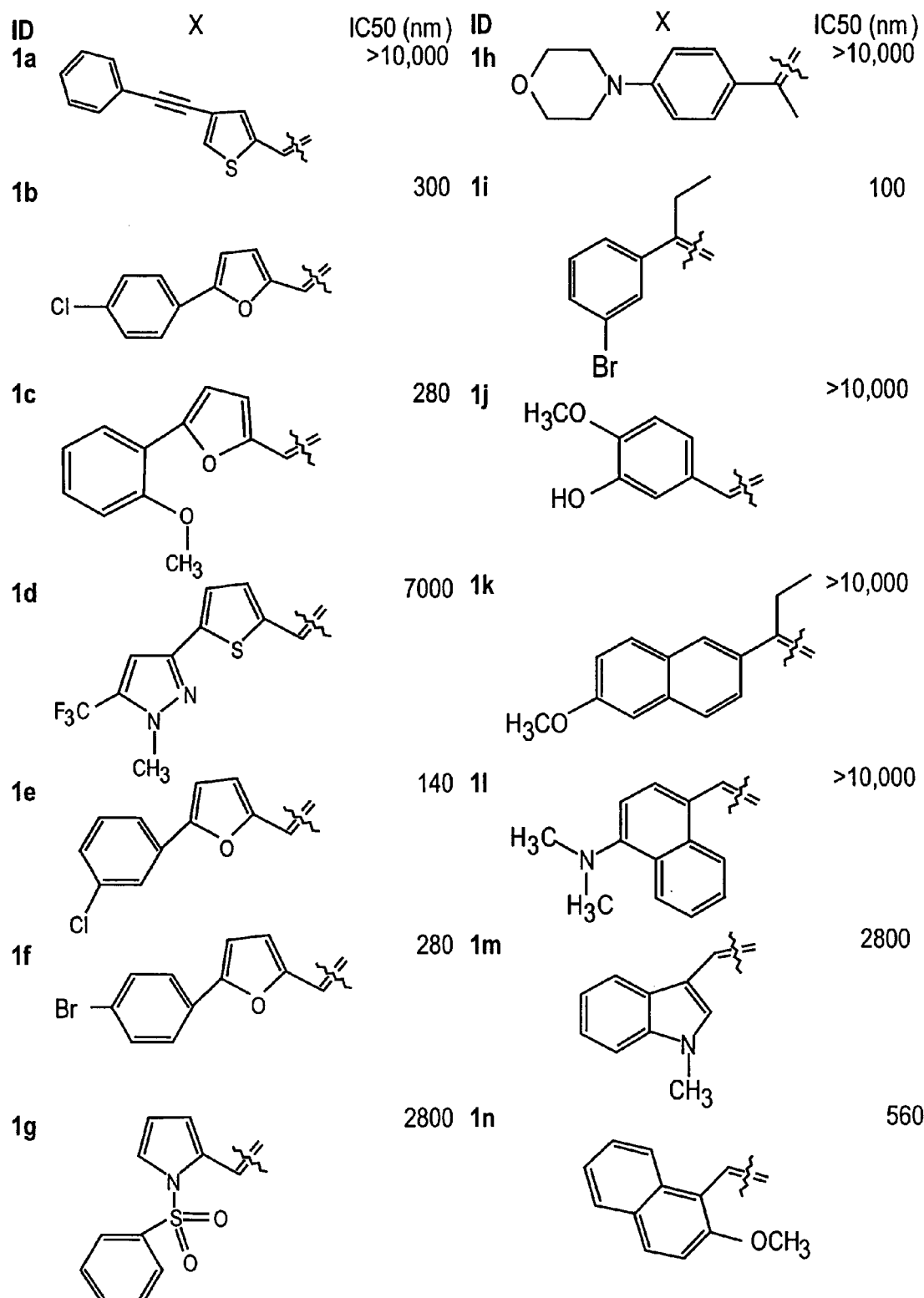
FIG. 2 shows the initial 14 thio semicarbazone compounds synthesized and their inhibition of cruzain activity as represented by IC50 values.

A library of Parke-Davis chemical compounds was screened. Forty-five compounds were identified as active against cruzain. We observed a semicarbazone scaffold common to several of the inhibitors (FIG. 1). To further explore the activity of the thio semicarbazone scaffold an initial group of 14 compounds were synthesized. Studies of noncovalent inhibitors of curzain, including bisaryl acylhydrazides and ureas, demonstrate that the most active compounds have a six-membered phenyl ring-five-membered heteroaromatic ring combination (6-5) in the aryl position. This feature was incorporated into some of the compounds. Some other alternatives in the aryl position were also tried including fused aromatic rings or single aromatic rings. Four of the 6-5 compounds (1b, 1c, 1e, 1f) have IC50 values below 300 nM. Two of the alternative compounds; (1i, 1n) were active at 100 and 560 nM against the enzyme, respectively (FIG. 2).

Figure 3:
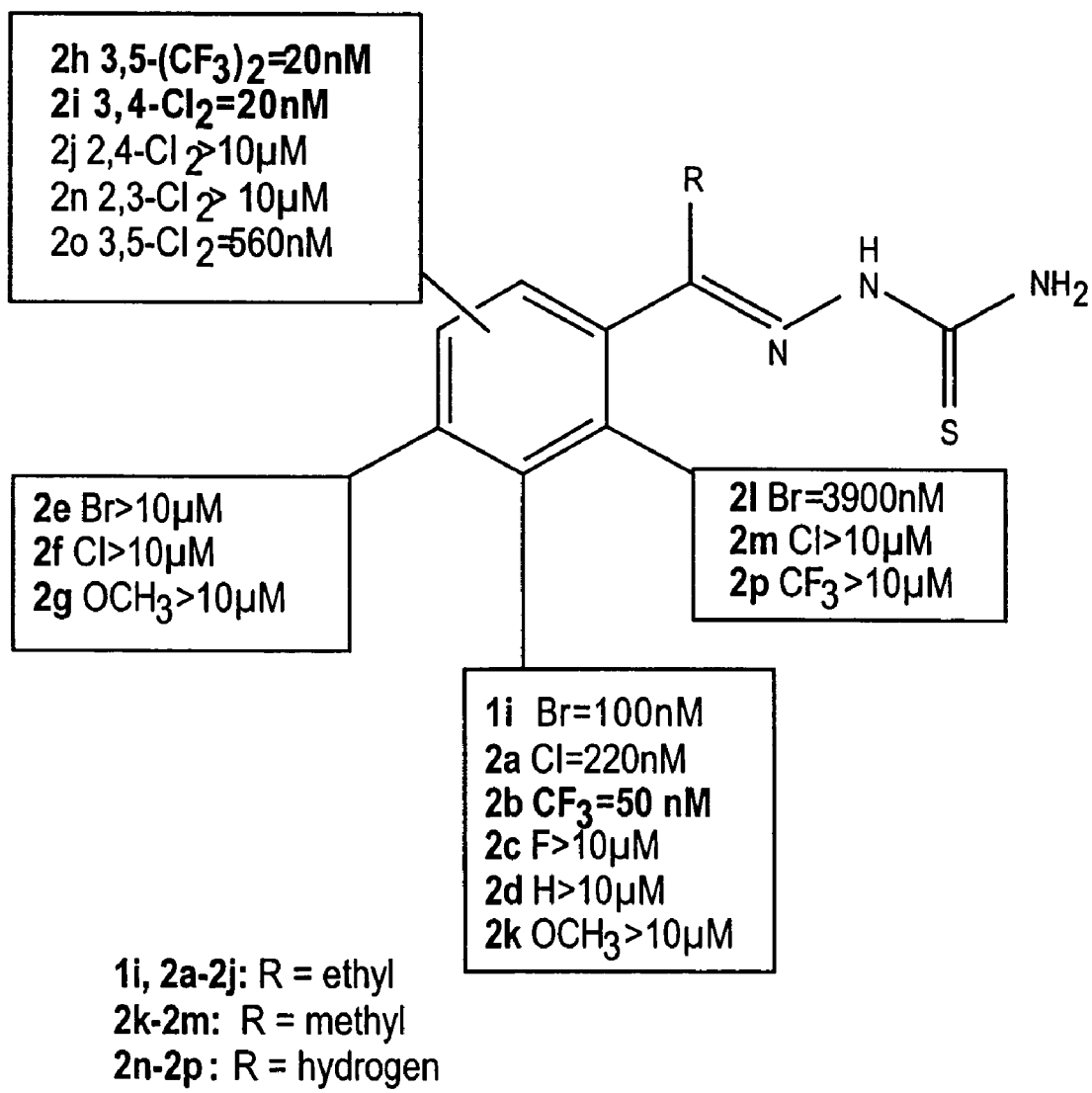
FIG. 3 shows how variation of the aryl substituents and position of the substituents effects different cruzain inhibitory capacities. Compounds in bold have lower (better) IC50 values than compound 1i.

Structure-Activity Relationship (SAR) Studies Aryl Group Activity (FIG. 3).

Figure 11:
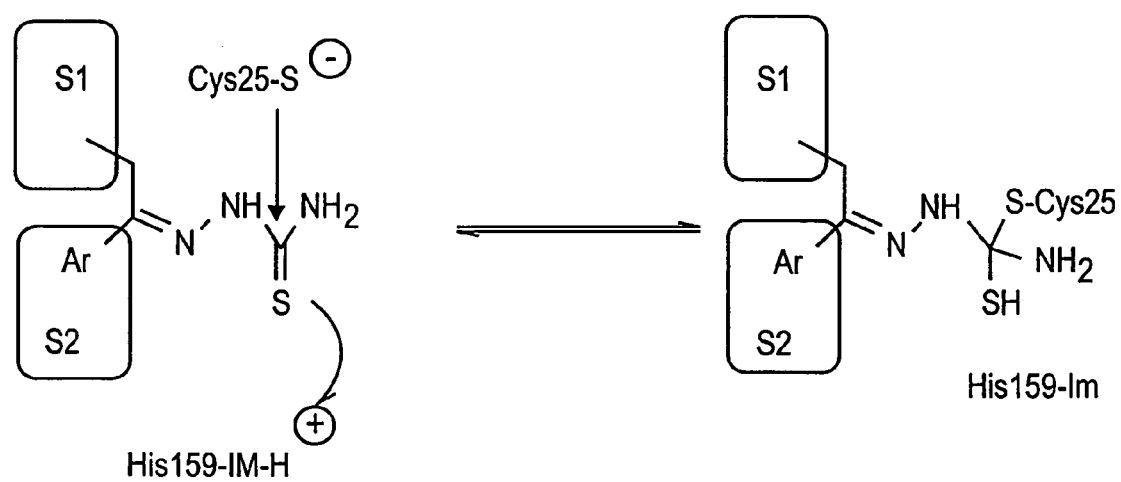
FIG. 11 shows a tridimensional depiction of the best calculated orientation of compound 1i in the active site of cruzain. The surface of the active site of cruzain is represented by gray dots. His159 and Cys25 are colored in green. Compound 1i is colored according to atom types: bromine, magenta; carbon, gray; hydrogen, white; nitrogen, blue; sulfur, yellow.

A series of 1i analogues with various substituents on the aryl moiety were synthesized. Compound 2d did not have any substitution on the aryl ring. Its activity dropped at least 2 orders of magnitude compared to that of 1i (samples with IC50 values greater than 10 µM were not tested further). C-2 substitution with bromine, chlorine, or trifluoromethyl groups resulted in poor activity. Though the compounds in FIG. 2 vary at C-5 (ethyl, methyl, or hydrogen), the differences in IC50 resulting from the C-5 differences are not significant compared to those resulting from the differences in the phenyl ring substitution as indicated by the SAR shown in FIG. 11. Among the C-3 variants, the trifluoromethyl substitution (2b) resulted in a better inhibitor compared to 1i with an IC50 of 50 nM. The chlorine substitution was well tolerated (compound 2a, 220 nM), but was not as potent as 1i. Fluorine or methoxy substitution at C-3 resulted in a loss of activity of more than 2 orders of magnitude. C-4 substitution with bromine, chlorine, and methoxy groups all resulted in a decrease of activity of more than 2 orders of magnitude. Several disubstituted analogues were synthesized. 3,4-Dichloro (2i) or 3,5-bis-(trifluoromethyl) (2h) substitution resulted in potent inhibitors with IC50 values of 20 nM, about a 5-fold increase in activity over 1i. The 3,5-dichloro substitution was also tolerated. Dichlorine substituents at C-2 (2,3-Cl$_2$ or 2,4-Cl$_2$) resulted in poor activity, consistent with the aforementioned observation that C-2 is a suboptimal site for substitution.

Figure 4:
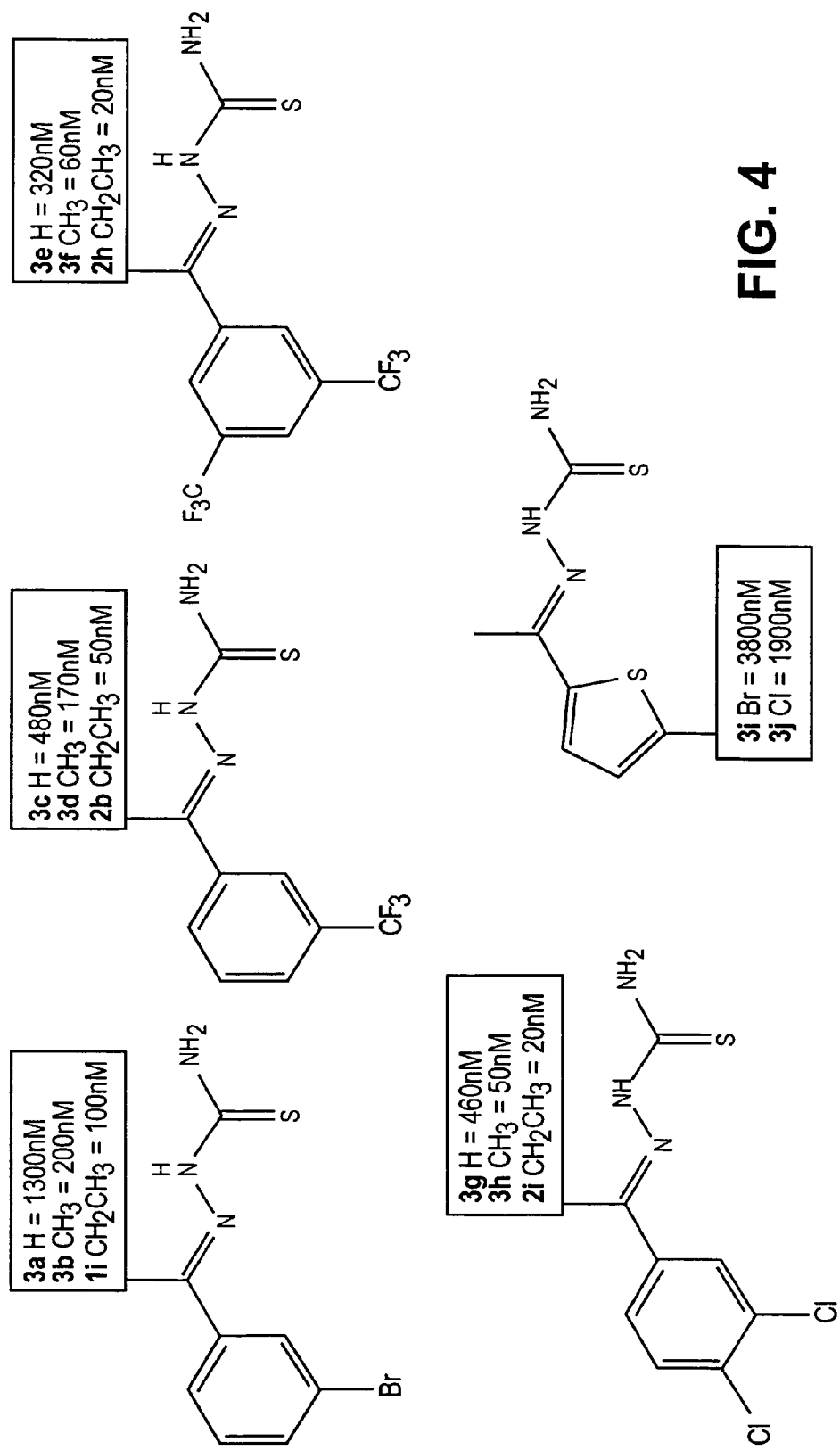
FIG. 4 shows that compound having a C-5 ethyl group inhibit cruzain more effectively than compounds with a C-5 methyl group or a C-5 hydrogen.

Varying Ethyl Groups at C-5 (FIG. 4).

The IC50 of the compounds decreased from 1300 nM for a hydrogen (3a) to 200 nM for a methyl (3b) to 100 nM for an ethyl group (1i) at C-5. The same trend was observed for other substituents such as trifluoromethyl, bis(trifluoromethyl), and dichloro groups. Compared to those of unsubstituted compounds and methyl-substituted compounds, the IC50 of ethyl-substituted compounds improved more than 10-fold and 2-3-fold, respectively. Changing the phenyl ring to bromo- or chloro-substituted thiophenes resulted in a significant loss of activity of ~20-fold.

Cyclized Pyrazoline Analogues (FIG. 5).

A set of analogues with the C-5 ethyl group attached to the C-3 nitrogen to form a pyrazoline ring was synthesized to investigate the influence of the restricted flexibility and the impact of substitution on the C-3 nitrogen. Compound 4a resulted in a 2-fold decrease in activity as compared to 1i. However, addition of a methyl group on the pyrazoline ring (4b) restored the activity. Compound 4b had an IC50 of 80 nM, slightly better than that of the parent compound 1i. Similar trends were observed in the chlorine-substituted (4c, 4d) and trifluoromethyl-substituted (4g, 4h) analogues. For dichloro substitutions, an additional methyl group in the ring (4f) reduced the activity. Limits in solubility may contribute to the decreased activity of this compound. Compound 4f has the poorest solubility in methanol compared to the others. Overall, there are five pyrazoline analogues (4b, 4e, 4f, 4g, and 4h) that have IC50 values better than that of 1i.

Figure 6:
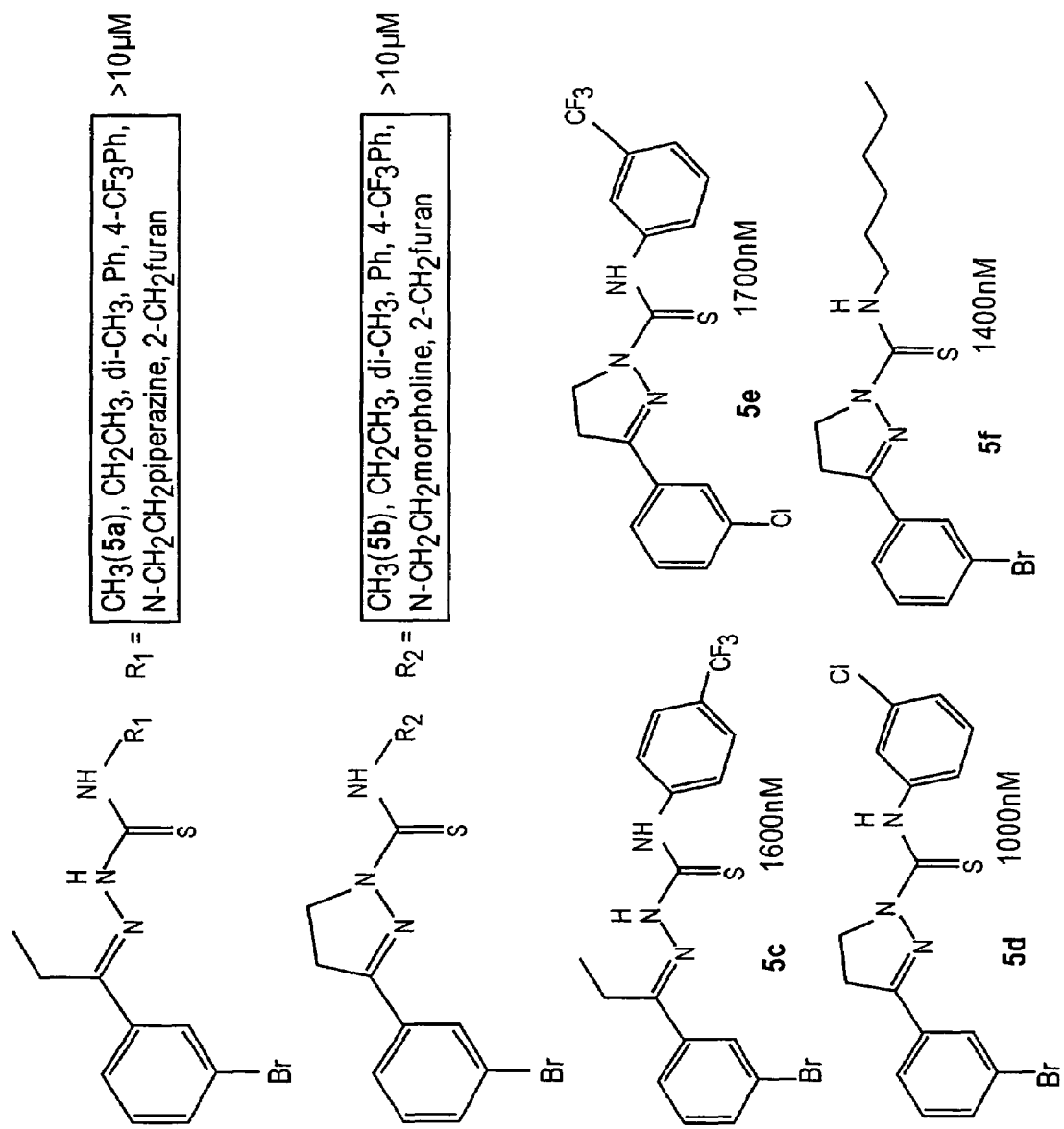
FIG. 6 shows that substitution on the N1 amino group results inhibitors with higher IC50 values in comparison to the IC50 value of compound 1i.

N1 NH2 Substitutions (FIG. 6).

A variety of noncyclized and cyclized pyrazoline thio semicarbazones substituted on the N1 amino group were synthesized. These included alkyl groups (e.g., methyl, dimethyl, ethyl, hexyl), aryl groups (e.g., phenyl, chlorophenyl, trifluoromethylphenyl), methylfuran, and ethylmorpholine. Most of the compounds had an IC50 greater than 10 µM. A few of them (5c, 5d, 5e, and 5f) had moderate activity between 1 and 2 µM.

C=S Double Bond (FIG. 7).

Semicarbazone analogues of the most active thio semicarbazones were synthesized. All of these compounds had IC50 values greater than 10 µM. This is evidence that the sulfur in the C=S double bond is critical for activity.

C=N4 Double Bond (Scheme 3).

Reduction of 1i by sodium borohydride generated the saturated C—N4 bond variant of 1i (7a). Compound 7a exhibited poor activity compared to 1i, indicating the importance of the double bond.

rigidity of the group, the activity varies. Propyl and butyl provide a flexible fit, resulting in good activity.

Summary of Protease Inhibition Assays

The thio semicarbazone series exhibited a specific and consistent structure-activity relationship. Reduction of the C=N4 bond or a change of the C=S bond into a C=O bond results in poor activity. For compounds with single phenyl rings, substitution at specific positions can lead to enhanced activity. The most potent compounds have at least one substituent group at C-3. Among the C-3 substituents, trifluoromethyl, bromine, and chlorine result in potent inhibitors while compounds with other groups have poor activity. Disubstitution with 3,4-dichlorine or 3,5-bis(trifluoromethyl) results in potent inhibitors of cruzain. By contrast, C-2 or C-4 substitution alone is not useful. Five compounds (2b, 2h, 2i, 3f, 3h) have better IC50 values than 1i. Compounds with the six phenyl-five heteroaromatic group also are effective inhibitors of cruzain. Ethyl substitution at C-5 is favorable over a broad range of compounds with different aryl substituents. Connection of the C-5 ethyl group and the N-3 into cyclized pyrazoline analogues resulted in compounds with potent activities. Some of the pyazoline compounds have improved IC50 values when compared with the noncyclized analogues.

Example 10

Inhibition of Rhodesain and Cathepsin B

The following example shows the activity of selected thio semi carbazone compounds against rhodesain, the major protease of *Trypanosoma brucei* and against human cathepsin B, a cancer and inflammatory disease target.

Enzyme assays to test the ability of thio semicarbazone compounds to inhibit the cysteine protease activity of rhodesain and cathepsin B were carried out as described for assays to test inhibition of protease activity by cruzain. In these assays, inhibition of cruzain is included as a positive control.

TABLE 1

Inhibition of Rhodesain and Cathepsin B

| compound | cathepsin B IC50 (µM) 5 min preincubation | cathepsin B IC50 (µM) 30 min preincubation | cruzain IC50 (µM) 5 min preincubation | rhodesain IC50 (µM) |
|---|---|---|---|---|
| guo4-52 | 5 | 1 | 0.01 | 0.03 |
| guo4-44 | >>10 | 10 | 0.03 | 0.052 |
| du2-79 | >>10 | >>10 | 0.08 | 0.07 |
| du5-13 | >>10 | 10 | 0.1 | 0.06 |
| du5-7 | >>10 | 10 | 0.01 | 0.03 |
| K002 | 0.5 | <0.1 | not done | |

Figure 14:
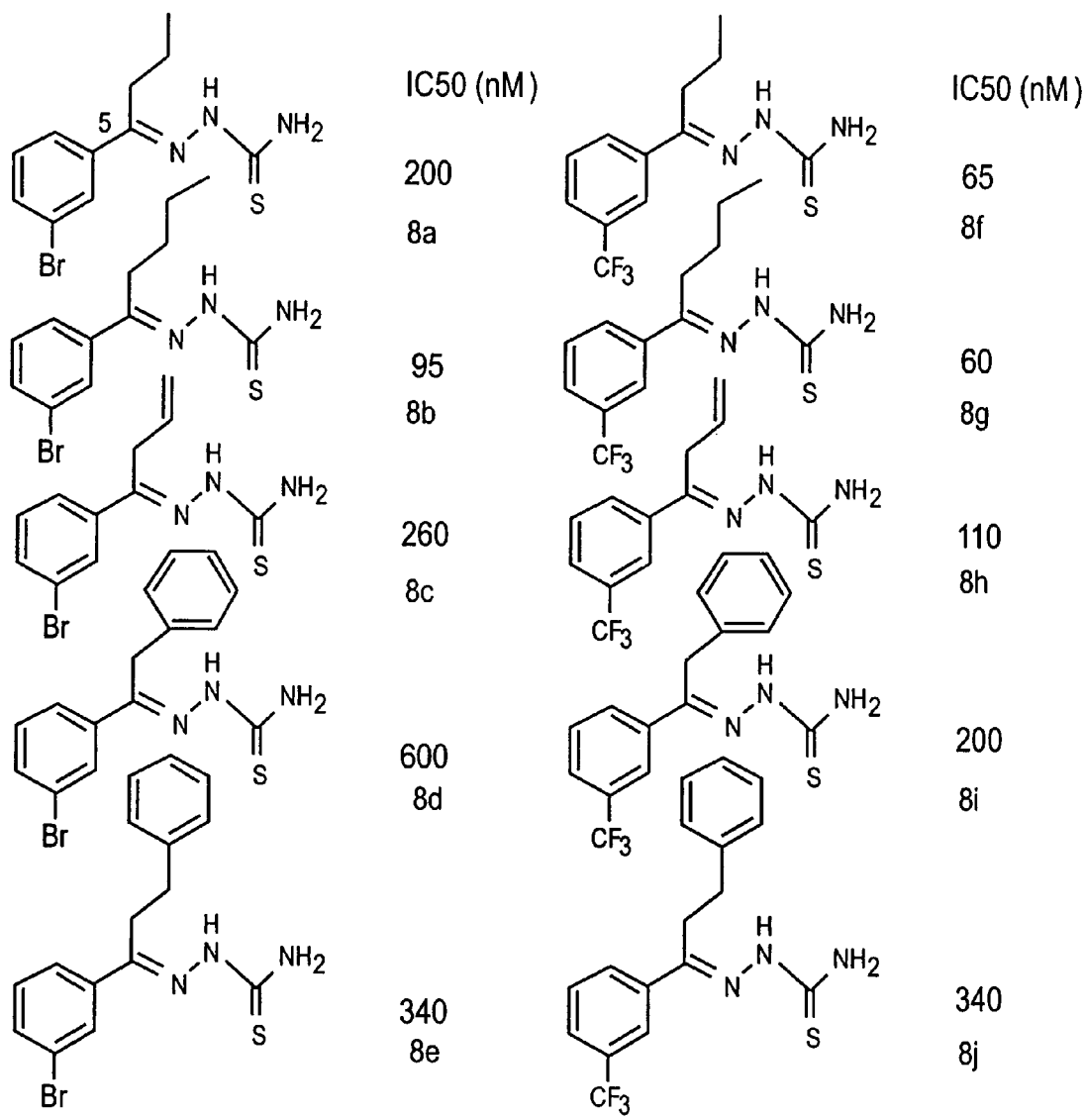
FIG. 14 shows the IC50s of the compounds with additional C5-side chain variations. This is consistent with our modeling efforts that show the C5-side chain occupying the shallow S1 pocket, and therefore accepting a wide range of groups without greatly decreasing the IC50s.

Inhibition to falcipain-2 and parasite *P. falciparum*
Compound 2i: IC50 150 nM on falcipain-2.
Compound 1i IC50 of parasite *P. falciparum* 16-32 µM Varying C5-groups with Longer Alkyl Chains and Aryl Groups (FIG. 14)

While the variation at C5 from H to $CH_3$ to $CH_2CH_3$ was obvious, longer alkyls such as propyl, butyl or other groups such as allyl, benzyl, phenylethyl group did not increase the $IC_{50}$ further, though generally all the compounds have good activity. This is consistent with our modeling results. Since the S1 pocket is small, the maximum interaction is reached by having approximately two carbons. While additional carbons simply project from the pocket. Depending on the sterics and Example 11

Anti-Trypanosomal Assays in Cell Culture

Methods

Drug Screening in Cell Culture. Mammalian cells are routinely cultured in RPMI-1640 medium supplemented with 5-10% heat-inactivated fetal calf serum (FCS) at 37° C. in 5% $CO_2$. The Y strain of *T. cruzi* is maintained by serial passage in bovine embryo skeletal muscle (BESM) cells. Infectious trypomastigotes are collected from culture supernatants. For drug assays, J774 macrophages were irradiated (5000 rad) and plated onto six-well tissue culture plates 24 h prior to infection with ~106 trypomastigotes/well. Parasites are removed 2 h postinfection, and the medium is supplemented with the appropriate cysteine protease inhibitor (10 µM). Inhibitor stocks (10 mM) in DMSO were stored at 4° C. J774 monolayers treated with a blank containing DMSO are used as a negative control, and monolayers treated with a known trypanocidal inhibitor, 10 µM N-methyl piperazine-Phe-homoPhe-vinyl sulfone phenyl (N-Pip-F-hF-VSPh) acted as a positive control (Engel et al., *J. Exp. Med.*, 188:725-734 (1998)). RPMI medium with or without inhibitor is replaced every 48 h. Cultures are maintained for up to 30 days and monitored daily by contrast phase microscopy. *T. cruzi* completed the intracellular cycle in 5-6 days in the untreated controls but was unable to survive in macrophages treated with N-Pip-F-hF-VSPh. The comparative effectiveness of each inhibitor was estimated from plots of the duration of the intracellular cycle of *T. cruzi* (days) in treated vs untreated control wells.

Results

In addition to their effect on enzymatic activity, we determined whether thio semithiocarbazones other than compound 1i entered cells and exerted a trypanocidal effect against this intracellular parasite.

Three (1i, 1e, 1f) of the most effective compounds were tested against intact trypanosomes in cell culture. Typically, infected host cells die within 5 days without treatment. In contrast infected host cells treated with compound 1e (5 µM) survived 10 days, but the therapeutic index associated with this compound was low, with toxicity to host cells observed at 10 µM. Infected host cells treated with compound 1f survived 14 days, but this compound crystallized in the cell culture medium. In other words, compounds 1e and 1f were trypanostatic. Compound 1i exhibited significant trypanocidal activity without toxicity to host cells or solubility problems. Infected cells treated with 1i at 10 µM were cured of trypanosomal infection. To confirm trypanocidal activity, infected cells were treated with 1i for three weeks and then 1i was removed from the cell culture. No parasites were observed in either the culture supernatants or host cells. Cells were healthy and parasite-free until the experiment was terminated at 6.5 weeks postinfection.

Encouraged by this result we explored compounds related to 1i in an effort to find more active, trypanocidal analogues.

The trypanocidal properties of representative compounds as judged by the survival of infected host cells is shown in FIG. 8. The toxicity of compounds to mammalian host cells was also evaluated in the assay. Of the five 3-bromo-substituted compounds, three (1i, 3b, 4b) exhibited a trypanocidal effect. No parasites were observed in supernatants or host cells after the inhibitors were removed at day 22. The 3-chloro-substituted compound 2a was also trypanocidal, but the two disubstituted compounds 2i and 2h were not, although one of them was trypanostatic for 20 days. Three more compounds from the initial group of thio semicarbazones were tested but were not effective. Toxicity (1c, 1n) or solubility (1b) appears to be a problem for some of the compounds tested in this latter group. Two moderate inhibitors with substitution on the N1 amino group (5c, 5d) had no effect on the parasites.

A second group of inhibitors having low IC50 values was evaluated by cell culture assay and these are shown in FIG. 9. Among these 10 compounds, two (4c, 4g) were inactive. Three were trypanostatic (3f, 3d, 4f). The remaining five compounds (2b, 3h, 4d, 4e, 4h) were trypanocidal and cure the infected cells. Altogether, nine compounds have been identified to be trypanocidal through the cell culture assay, indicating that the thio semicarbazone is a productive scaffold for antitrypanosomal therapy.

Summary of Cell Culture Anti-Trypanosomal Assays

Compounds that are potent cruzain inhibitors in vitro are not necessarily active in cell culture. Antiparasitic inhibitors must be able to cross the macrophage's cell membrane and cross the parasite's cytoplasm in sufficient quantity to significantly inhibit cruzain without killing the host cell. Nine compounds in the thio semicarbazone series (three single-phenyl-ring-substituted compounds (1i, 2a, 2b), two of the methyl-substituted thio semicarbazones (3b, 3h), and four pyrazoline analogues (4b, 4d, 4e, 4h) are trypanocidal.

Lipinski described desired ranges for certain properties thought to be important for pharmacokinetics and drug development. They are C log P<5, number of hydrogen bond donors ≦5, number of hydrogen bond acceptors ≦10, and molecular weight <500 (Lipinski, C. A. et al., *Adv. Drug Delivery Rev.*, 23:3-25 (1997)). A compound that fulfills at least three out of the four criteria adheres to Lipinski's rule. Table 1 lists such properties of the nine trypanocidal compounds. All of our most potent antiparasitic agents are fully compatible with Lipinski's rule.

TABLE 1

The Trypanocidal Compounds Have Physical Properties Compatible with Reasonable Pharmacokinetics and Drug Availability

| ID | mol wt | C log P | no. of H bond acceptors | no. of H bond acceptors | no. of Criteria met |
|---|---|---|---|---|---|
| rule | <500 | <5 | <5 | <10 | at least 3 |
| 1i | 286 | 3.79 | 3 | 3 | all |
| 2a | 242 | 3.64 | 3 | 3 | all |
| 2b | 275 | 3.81 | 3 | 3 | all |
| 3b | 272 | 3.26 | 3 | 3 | all |
| 3h | 262 | 3.71 | 3 | 3 | all |
| 4b | 298 | 4.33 | 2 | 3 | all |
| 4d | 254 | 4.18 | 2 | 3 | all |
| 4e | 274 | 4.25 | 2 | 3 | all |
| 4h | 287 | 4.35 | 2 | 3 | all |

*For Structures, See FIGS. 8 and 9

Example 12

Mechanism of Inhibition

Figure 10:
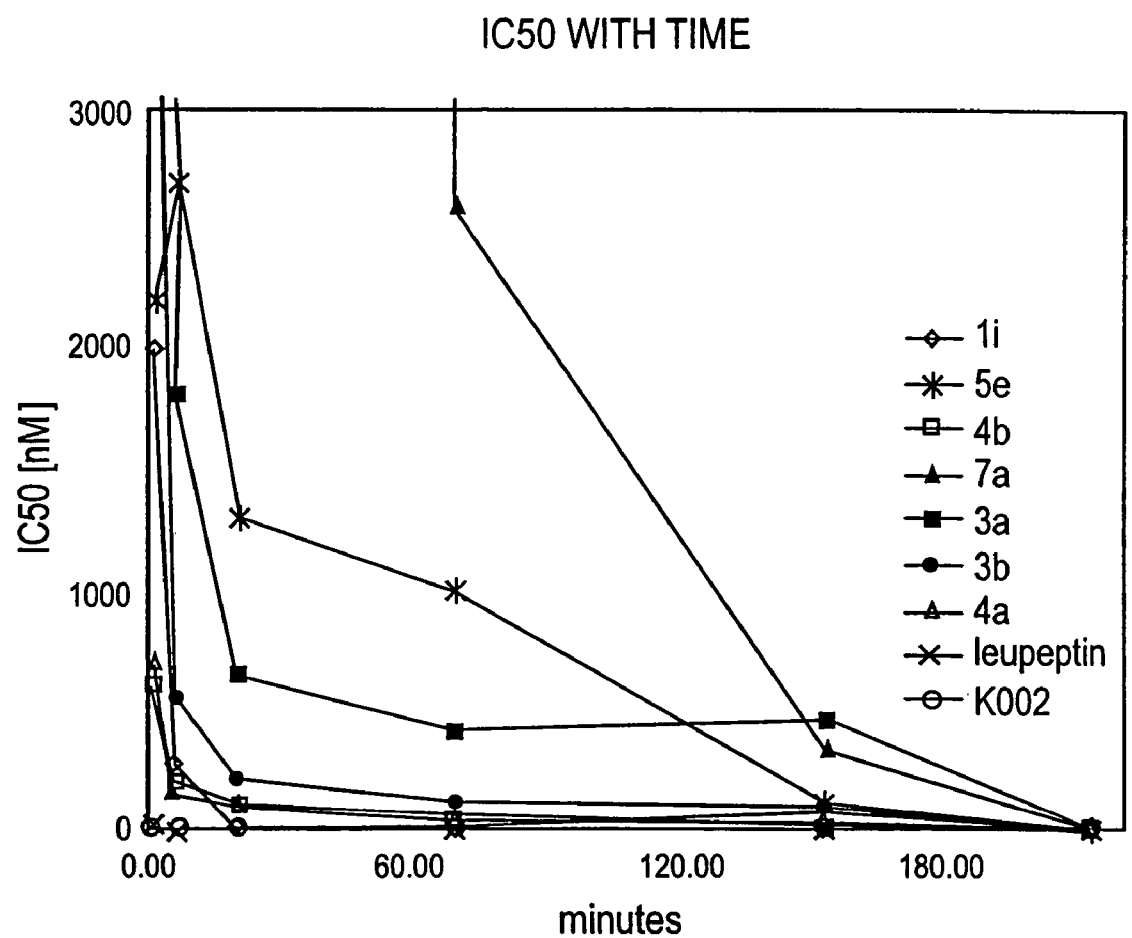
FIG. 10 shows a line graph depicting IC50 values versus time. The data of representative thio semicarbazones are shown.

The most active thio semicarbazone compounds including the pyrazoline analogues are time-dependent inhibitors. This indicates that inhibition by the thio semicarbazone series is mechanism-based. A variety of compounds including some of the ones with moderate to poor activity were chosen for a more detailed study of time-dependent inhibition (FIG. 10). A known irreversible inhibitor, K002 (morpholino urea-Phe-homoPhe-vinyl sulfone benzene; Axys Pharmaceuticals Inc., South San Francisco, Calif.), and a known reversible covalent inhibitor, leupeptin, were used as controls for the thio semicarbazones. Both controls were rapidly time-dependent. Inhibitors with a free N1 amino group such as 1i, 4b, 3a, 3b, and 4a are time-dependent. Even some of the weak inhibitors such as 5e and 7a showed time dependency. The time dependency of 7a indicates that the C=N4 double bond is not the site for covalent bond formation. Thus, the only logical site for covalent interaction with cruzain in 7a is the C=S double bond.

Example 13

Molecular Modeling

Methods

DOCK 4.0.1 is used to position putative inhibitors in the enzyme active site and score the quality of the interactions of inhibitors with cruzain (Ewing, T. J. A. et al., J. Comput. Chem., 18:1175-1189 (1997)). The procedure for constructing the molecular surface and the energy grid of the active site of cruzain is found in Du, et al. (*Chem. Biol.* (2000) 7:733). The C log P values are calculated for each compound using the software C Log P 4.61 (Daylight Chemical Information Systems, Santa Fe, N. Mex.) on the basis of the work of Hansch (Hansch. C. et al., Substituent Constants for Correlation Analysis in Chemistry and Biology, Wiley-Interscience: New York, (1979)).

Results

Figure 12:
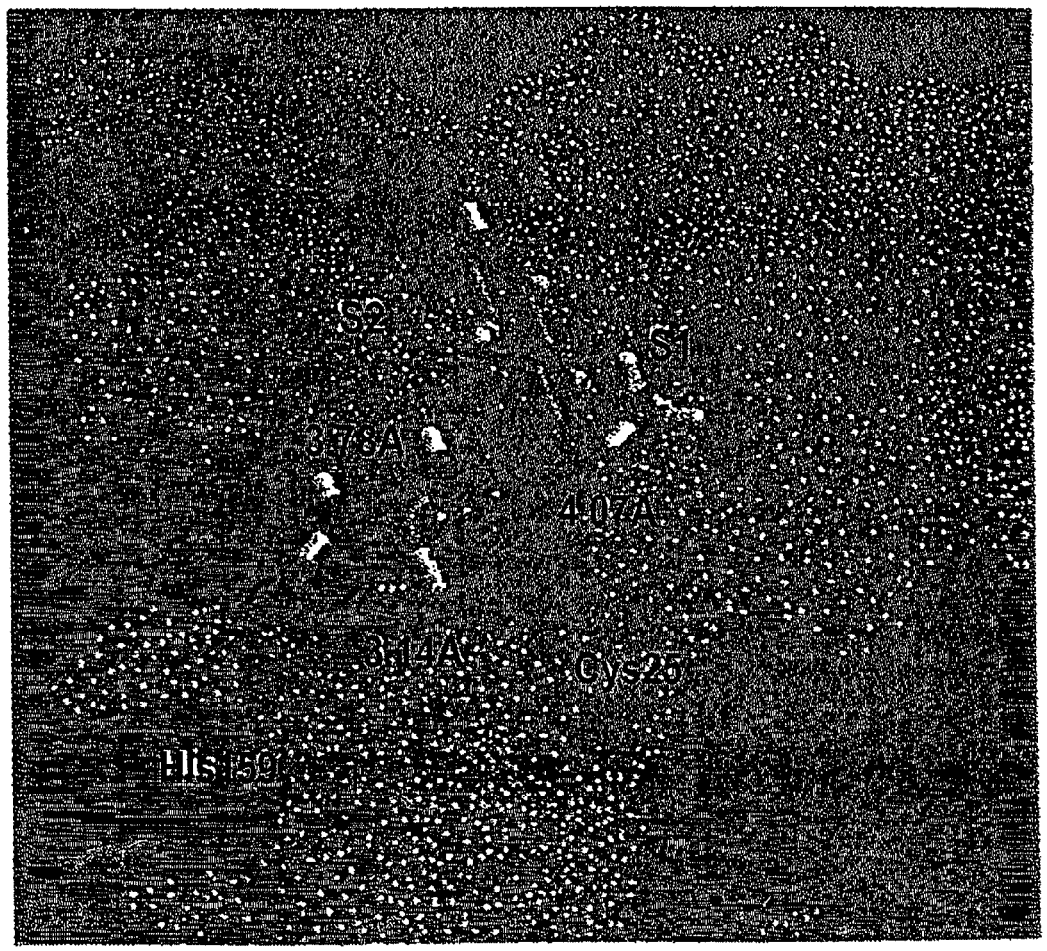
FIG. 12 shows a proposed mechanism of reversible covalent interaction between thio semicarbazones and cruzain based on experimental and modeling results.

To further understand the mechanism of interaction, computational tools were used to dock compound 1i into the active site of cruzain. These models provide insight into the activity of the cruzain inhibitors. The calculated best orientation of 1i with cruzain is shown in FIG. 3. The bromophenyl portion of 1i is oriented toward the deep S2 pocket. Such an interaction is not ideal as judged by the modeling effort. We anticipate that the ethyl group fits into the shallow S1 pocket, while the rest of the thio semicarbazone scaffold is positioned close to Cys25 and His159. The distance between one of the His159 protons and the sulfur in the thio semicarbazone is calculated to be 3.14 Å. In this docked orientation, the distance between the Cys25 thiolate and the carbon (C2) attached to sulfur is 3.78 Å and the distance between the Cys25 thiolate and the carbon in C=N4 is 4.07 Å. The separation between N4 and the proton of His 159 (4.31 Å) is not compatible with a direct interaction. Therefore, this orientation of 1i suggests that the covalent attack of the Cys25 on 1i is directed toward the C2=S bond, consistent with the time dependency of 7a. The attack on the C2=S bond would be assisted by the transfer of the His159 proton to the thio semicarbazone sulfur (FIG. 12).

If the ethyl group fits into the S1 pocket, this would explain the preference for an ethyl group over a methyl group or a hydrogen in the S1 pocket. The unsubstituted pyrazoline ring analogues have a methyl group equivalent on C-4. This observation is consistent with the result that the pyrazoline analogue 4a has 2-fold lower activity when compared to the parent ethyl compound 1i. Upon addition of a methyl group to the C4 position on the pyrazoline ring, this analogue resembles the original ethyl substituent and its activity is restored.

When the semicarbazone analogue 6a was docked into the active site, none of the top 20 orientations were similar to that of 1i. Most orient the semicarbazone portion toward the S2 site and the aryl group toward the S' site. In other words, the modeling suggests that the electronic and volumetric difference between a sulfur and an oxygen atom may make a substantial difference. This is consistent with the substantial activity difference between compounds 6a and 1i.

Example 14

In Vitro Data for Compounds

Thio semicarbazones have been tested against falcipain 2, which is the cysteine protease of parasites related to malaria. Of those tested, compound 2i is the most promising, with an IC50 of 150 nM. The WHO (World Health Organization) helped to screen compound 1i against a couple of parasite strains. It has activity against *T. cruzi* and *P. falciparum* parasites. See FIG. 15.

What is claimed is:
1. A compound having the formula:

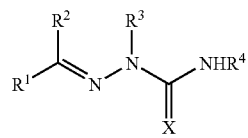

wherein
$R^1$ is

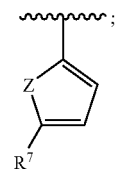

$R^2$ is a member selected from the group consisting of H, and substituted or unsubstituted lower alkyl;
$R^3$ is a member selected from the group consisting of H, and substituted or unsubstituted lower akyl;
$R^4$ is a member selected from H and substituted or unsubstituted lower alkyl;
$R^7$ is phenyl substituted with 1-5 members selected from the group consisting of Cl and Br;
X is S; and
Z is O.
2. The compound according to claim 1, wherein $R^2$ is a member selected from the group consisting of H, $CH_3$, and $CH_2CH_3$.
3. A pharmaceutical composition comprising a therapeutically effective amount of a compound of claim 1 and a physiologically acceptable carrier.
4. The pharmaceutical composition of claim 3, wherein the composition is formulated for oral administration.
5. The pharmaceutical composition of claim 3, wherein the composition is formulated for parenteral administration.

6. The pharmaceutical composition of claim 3, said composition comprising a therapeutically effective amount of a compound selected from the group consisting of:
   a) 5-(4-chlorophenyl)-2-furancarboxaldehyde Thio Semicarbazone (1b),
   b) 5-(3-chlorophenyl)-2-furancarboxaldehyde (1 e), and
   c) 5-(4-bromophenyl)-2-furancarboxaldehyde (1 f).

7. The compound of claim 1 selected from the group consisting of:
   a) 5-(4-chlorophenyl)-2-furancarboxaldehyde Thio Semicarbazone (1 b),
   b) 5-(3-chlorophenyl)-2-furancarboxaldehyde (1 e), and
   c) 5-(4-bromophenyl)-2-furancarboxaldehyde (1 f).

* * * * *